(12) United States Patent
Berme

(10) Patent No.: US 8,915,149 B1
(45) Date of Patent: *Dec. 23, 2014

(54) FORCE MEASUREMENT SYSTEM

(71) Applicant: Bertec Corporation, Columbus, OH (US)

(72) Inventor: Necip Berme, Worthington, OH (US)

(73) Assignee: Bertec Corporation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/015,535

(22) Filed: Aug. 30, 2013

Related U.S. Application Data

(63) Continuation-in-part of application No. 13/348,506, filed on Jan. 11, 2012, now Pat. No. 8,544,347.

(51) Int. Cl.
   *G01D 7/00* (2006.01)
   *G01L 1/22* (2006.01)

(52) U.S. Cl.
   CPC .............................. *G01L 1/22* (2013.01)
   USPC ................................... 73/862.041

(58) Field of Classification Search
   USPC ................................... 73/862.041
   See application file for complete search history.

(56) References Cited

U.S. PATENT DOCUMENTS

| | | | |
|---|---|---|---|
| 4,739,848 A | 4/1988 | Tulloch | |
| 4,800,973 A * | 1/1989 | Angel | 177/211 |
| 4,880,069 A | 11/1989 | Bradley | |
| 5,708,236 A | 1/1998 | Shaanan et al. | |
| 5,750,937 A * | 5/1998 | Johnson et al. | 177/25.11 |
| 6,038,488 A | 3/2000 | Barnes et al. | |
| 6,052,114 A | 4/2000 | Morifuji | |
| 6,113,237 A | 9/2000 | Ober et al. | |
| 6,152,564 A | 11/2000 | Ober et al. | |
| 6,222,137 B1 | 4/2001 | Handford | |
| 6,295,878 B1 | 10/2001 | Berme | |
| 6,354,155 B1 | 3/2002 | Berme | |
| 6,389,883 B1 | 5/2002 | Berme et al. | |
| 6,437,257 B1 * | 8/2002 | Yoshida | 177/199 |

(Continued)

OTHER PUBLICATIONS

Cutlip, R. et al., A comparison of different postures for scaffold end-frame disassembly, Applied Ergonomics, Oct. 2, 2000, vol. 31, Issue 5, pp. 507-513.

(Continued)

*Primary Examiner* — Lisa Caputo
*Assistant Examiner* — Octavia Hollington
(74) *Attorney, Agent, or Firm* — The Law Office of Patrick F. O'Reilly III, LLC

(57) ABSTRACT

A dual force plate system having two independent measurement surfaces is disclosed herein. The dual force plate system includes a first plate component having a first measurement surface for receiving a first portion of a body of a subject, a second plate component having a second measurement surface for receiving a second portion of the body of the subject, a first force transducer element operatively coupled to the first plate component, a second force transducer element operatively coupled to the second plate component, and a third force transducer element operatively coupled to both the first plate component and the second plate component. A force plate system for computing a center of gravity of a subject is also disclosed herein. In addition, a method for determining the center of gravity for a subject disposed on a force measurement assembly is described herein.

18 Claims, 29 Drawing Sheets

(56) References Cited

U.S. PATENT DOCUMENTS

| | | | |
|---|---|---|---|
| 6,797,894 B2 * | 9/2004 | Montagnino et al. | 177/238 |
| 6,812,414 B2 | 11/2004 | Nakagawa | |
| 6,936,016 B2 | 8/2005 | Berme et al. | |
| 7,418,875 B2 | 9/2008 | Kohno et al. | |
| 7,989,713 B2 | 8/2011 | Hulburt et al. | |
| 7,994,440 B2 | 8/2011 | Oseko et al. | |
| 8,030,582 B2 * | 10/2011 | Tanida et al. | 177/1 |
| 8,152,640 B2 | 4/2012 | Shirakawa et al. | |
| 8,181,541 B2 | 5/2012 | Berme | |
| 8,204,710 B2 * | 6/2012 | Walthert | 702/101 |
| 8,315,822 B2 | 11/2012 | Berme et al. | |
| 8,315,823 B2 | 11/2012 | Berme et al. | |
| 8,444,580 B2 * | 5/2013 | Ochi et al. | 601/27 |
| 2003/0216656 A1 | 11/2003 | Berme et al. | |
| 2008/0228110 A1 | 9/2008 | Berme | |
| 2011/0277562 A1 | 11/2011 | Berme | |
| 2012/0266648 A1 | 10/2012 | Berme et al. | |
| 2012/0271565 A1 | 10/2012 | Berme et al. | |

OTHER PUBLICATIONS

First office action on the merits (Non-Final Rejection) in U.S. Appl. No. 13/348,506, mailed on Jan. 30, 2013.

Notice of Allowance in U.S. Appl. No. 13/348,506, mailed on Jun. 11, 2013.

* cited by examiner

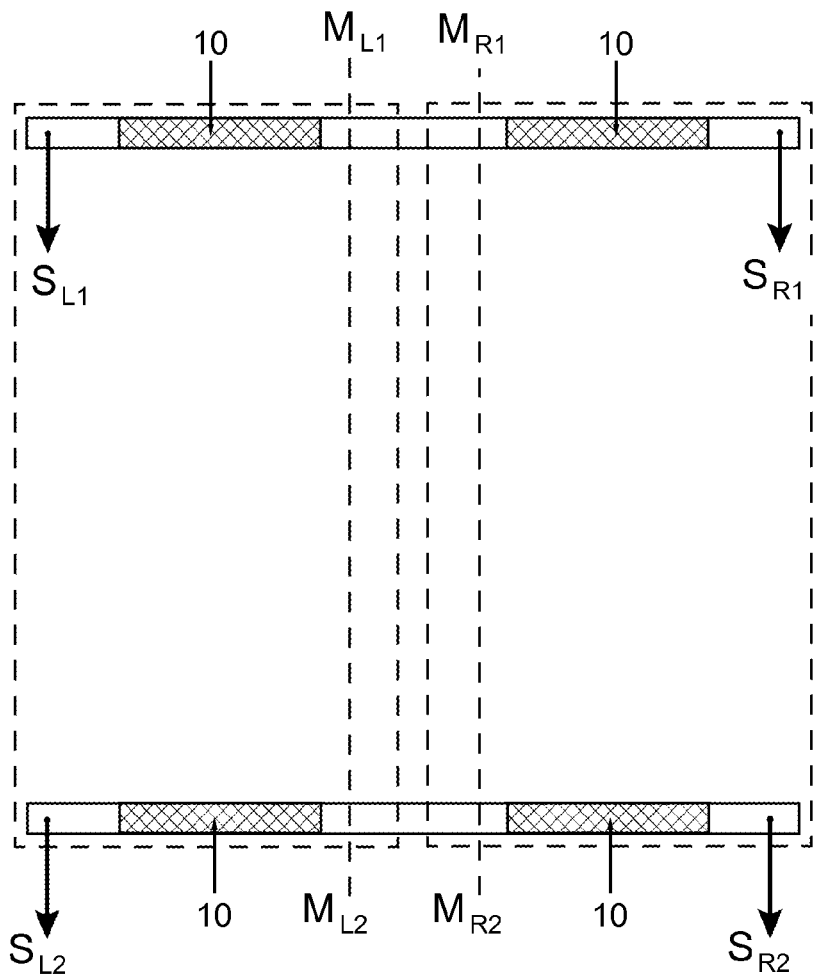
FIG. 26
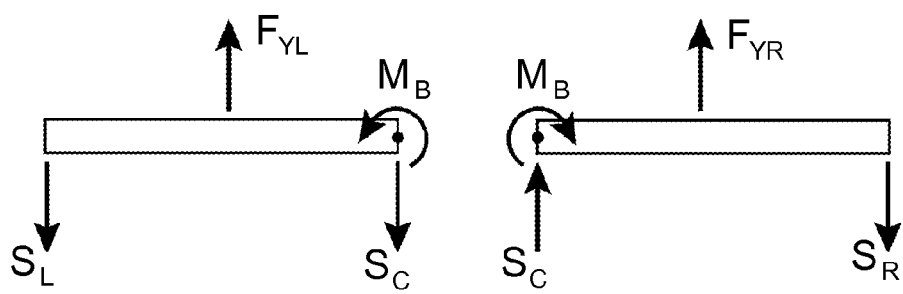
FIG. 27A  FIG. 27B

FORCE MEASUREMENT SYSTEM

CROSS-REFERENCE TO RELATED APPLICATIONS

This patent application is a continuation-in-part application, which is co-pending with, and claims priority from, U.S. Non-Provisional patent application Ser. No. 13/348,506, entitled "Force Measurement System Having a Plurality of Measurement Surfaces", filed on Jan. 11, 2012, which is incorporated by reference herein in its entirety by this reference thereto.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to force measurement systems. More particularly, the invention relates to a force measurement system that is particularly useful in the assessment of the balance of a subject.

2. Background and Description of Related Art

Force measurement systems are utilized in various fields to quantify the reaction forces and moments exchanged between a body and support surface. For example, in biomedical applications, force measurement systems are used for gait analysis, assessing balance and mobility, evaluating sports performance, and assessing ergonomics. In order to quantify the forces and moments resulting from the body disposed thereon, the force measurement system includes some type of force measurement device. Depending on the particular application, the force measurement device may take the form of a balance plate, force plate, jump plate, an instrumented treadmill, or some other device that is capable of quantifying the forces and moments exchanged between the body and the support surface.

A balance assessment of a human subject is frequently performed using a specialized type of a force plate, which is generally known as a balance plate. A balance plate is a sensitive weighing scale, which in addition to measuring the weight of the subject, also measures the point of application of the weight. Typically, this is achieved by having either three or four instrumented feet, each measuring the force transmitted through it. Then, based on how much force each foot carries, the point of application of the total force (i.e., the body weight is calculated). A typical use of a balance plate involves monitoring the manner in which this point of application of the force (i.e., the center of pressure) changes as the subject stands on the plate. For a quietly standing subject, the center of pressure variation is an indication of the amount of physiological sway that the subject experiences. Generally, a small center of pressure variation demonstrates that the subject is essentially stable, whereas a large center of pressure variation in quiet stance is interpreted as an indication that the subject may have difficulty maintaining his or her own balance, and may be in danger of sustaining a fall in normal daily living. Balance plates frequently are used in clinics and assisted-living environments by a clinicians and/or physical therapists who regularly carry the plate from one facility to another. Thus, it is highly desirable for a balance plate to be readily portable.

During a balance assessment, if it is desired to make independent measurements under each foot of a subject, two balance plates are typically either placed side-by-side or mounted on a common base. This arrangement permits a determination of the weight that is carried by each leg of the subject, and if there is a deficiency in one of the legs. However, using two separate plates requires carrying additional hardware. Also, the operator has to make sure that the plates are not touching one another as the patient steps on and off the system so that an accurate measurement of each leg can be obtained. When two plates are mounted on one common base, the system becomes significantly heavier, and thus, more difficult to transport. Both conventional two plate systems also have the disadvantage that measurement from each plate is recorded independently, and poses not only an inconvenience, but also increases the possibility of inadvertently mixing the left and right signals.

Also, because many subjects that are tested on a balance plate have a balance disorder or a potential balance problem, it is very important that subjects are able to easily step on and off of the plate. Thus, it is highly desirable for the balance plate to have as low a profile as possible. Although, on a conventional balance plate, the force measuring feet are placed underneath the surface on which the patient stands, which increases the overall height of the instrument and consequently makes it more difficult for a patient having balance disorders to step on and off the plate.

Static postural control (i.e., static balance) has commonly been modeled using an inverted pendulum. The model assumes rotation about the ankle joint and that most movement associated with postural control occurs in the anterior-posterior (forward/backward) direction. Two critical components of this model are the center of pressure (COP) and center of gravity (COG). As such, when assessing the balance of a subject, it is often important to analyze a subject's center of gravity, as well as the subject's center of pressure. While the center of pressure describes the point at which all resultant ground reaction forces act, the center of gravity is the location of the subject's center of mass projected straight down onto the surface of the balance plate. Direct measurement of the center of gravity is not possible by using a balance plate alone; however, it has been derived based on the movement of the center of pressure. Conventional balance systems utilize a filtering technique that provides an approximation of the center of gravity location. This filtering technique uses a 2nd order, low-pass Butterworth filter with a cutoff frequency of less than 1 Hertz (<1 Hz). The center of pressure data ($COP_x$, $COP_y$) is passed through this filter to come up with the approximation for the center of gravity location ($COG_x$, $COG_y$). This method of filtering affects the data in two ways: (1) the data is smoothed and slightly reduced in amplitude, and (2) a small time shift is added into the center of gravity data, causing it to fall more in line with the theoretical inverted pendulum model. Overall, the resulting filtered data has a slightly smaller amplitude and moves slightly out of sync with the center of pressure. Because this method of filtering only results in rough approximations of the subject's center of gravity over time, it is unable to determine the subject's center of gravity with the requisite accuracy.

What is needed, therefore, is a force measurement system that is in the form of a single force plate having two or more independent measurement surfaces for assessing the balance of a subject. Moreover, a force measurement system is needed that is readily portable, and thus, easy for an operator to transport from place to place. Additionally, a need exists for a force measurement system that has a low profile so that it is easier for subjects, such as patients having balance disorders or potential balance problems to step on and off the apparatus. Furthermore, a force measurement system is needed that is capable of accurately determining the center of gravity for a subject disposed thereon.

BRIEF SUMMARY OF EMBODIMENTS OF THE INVENTION

Accordingly, the present invention is directed to a force measurement system that substantially obviates one or more problems resulting from the limitations and deficiencies of the related art.

In accordance with one aspect of the present invention, there is provided a dual force plate system having two independent measurement surfaces, which includes: a first plate component having a first measurement surface for receiving a first portion of a body of a subject, a first opposed surface that is disposed generally opposite to the first measurement surface, and a plurality of lateral surfaces that extend between the first measurement surface and the first opposed surface; a second plate component having a second measurement surface for receiving a second portion of the body of the subject, a second opposed surface that is disposed generally opposite to the second measurement surface, and a plurality of lateral surfaces that extend between the second measurement surface and the second opposed surface, the second plate component being spaced apart from the first plate component by a gap; a first force transducer element operatively coupled to either the first opposed surface of the first plate component or to one of the lateral surfaces of the first plate component, the first force transducer element configured to output at least one first quantity that is representative of a shear force being applied to the first measurement surface; a second force transducer element operatively coupled to either the second opposed surface of the second plate component or to one of the lateral surfaces of the second plate component, the second force transducer element configured to output at least one second quantity that is representative of a shear force being applied to the second measurement surface; and a third force transducer element operatively coupled to either the first opposed surface of the first plate component and the second opposed surface of the second plate component, or to one of the lateral surfaces of the first plate component and one of lateral surfaces of second plate component, the third force transducer element extending across the gap between the first plate component and the second plate component, the third force transducer element configured to output at least one third quantity that is representative of a load being transferred between the first plate component and the second plate component.

In a further embodiment of this aspect of the present invention, either the first and third force transducer elements are both operatively coupled to the first opposed surface of the first plate component, or the first and third force transducer elements are both operatively coupled to the same lateral side of the first plate component.

In yet a further embodiment, either the second and third force transducer elements are both operatively coupled to the second opposed surface of the second plate component, or the second and third force transducer elements are both operatively coupled to the same lateral side of the second plate component.

In still a further embodiment, the dual force plate system further comprises a fourth force transducer element laterally spaced apart from the first force transducer element, the fourth force transducer element operatively coupled to either the first opposed surface of the first plate component or to another one of the lateral surfaces of the first plate component, the fourth force transducer element configured to output at least one fourth quantity that is representative of a shear force being applied to the first measurement surface; a fifth force transducer element laterally spaced apart from the second force transducer element, the fifth force transducer element operatively coupled to either the second opposed surface of the second plate component or to another one of the lateral surfaces of the second plate component, the fifth force transducer element configured to output at least one fifth quantity that is representative of a shear force being applied to the second measurement surface; and a sixth force transducer element laterally spaced apart from the third force transducer element, the sixth force transducer element operatively coupled to either the first opposed surface of the first plate component and the second opposed surface of the second plate component, or to another one of the lateral surfaces of the first plate component and another one of lateral surfaces of second plate component, the sixth force transducer element configured to output at least one sixth quantity that is representative of a load being transferred between the first plate component and the second plate component.

In yet a further embodiment, the first, second, and third force transducer elements are generally symmetrically arranged with respect to the fourth, fifth, and sixth force transducer elements.

In still a further embodiment, the first force transducer element, the second force transducer element, and the third force transducer element are each part of a continuous beam force transducer assembly having a longitudinal axis, the first, second and third force transducer elements being spaced apart along the longitudinal axis of the continuous beam force transducer assembly and each of the first, second and third force transducer elements intersecting the longitudinal axis of the continuous beam force transducer assembly; and wherein the continuous beam force transducer assembly extends substantially the combined length of the first and second opposed surfaces of the first and second plate components, or substantially the combined length of the lateral surfaces of the first and second plate components, to which the first and second force transducer elements are respectively coupled.

In yet a further embodiment, the first force transducer element is mounted in a cantilevered manner from the first plate component and the second force transducer element is mounted in a cantilevered manner from the second plate component.

In still a further embodiment, the dual force plate system further comprises a data processing device operatively coupled to the first force transducer element, the second force transducer element, and the third force transducer element, the data processing device configured to receive the first, second, and third quantities that are representative of the loads being applied to the first measurement surface, the second measurement surface, and transferred between the first and second plate components, respectively, and to convert the first, second, and third quantities into separate output loads for each of the first plate component and the second plate component.

In yet a further embodiment, the first force transducer element and the second force transducer element each comprise one or more apertures disposed therein and one or more pluralities of strain gages disposed on outer surfaces thereof, the outer surfaces of each force transducer element on which each of the one or more pluralities of strain gages are disposed being generally opposite to an inner surface of each of the one or more apertures.

In still a further embodiment, a continuous gap is provided between the first plate component and the second plate component so as to prevent interaction between the two plate components.

In accordance with another aspect of the present invention, there is provided a force plate system, which includes: a force measurement assembly configured to receive a subject, the force measurement assembly having a surface for receiving at least one portion of the body of the subject; at least one force transducer, the at least one force transducer configured to sense one or more measured quantities and output one or more signals that are representative of a load being applied to the surface of the force measurement assembly by the subject; and a data processing device configured to convert the one or more signals that are representative of the load being applied to the surface of the force measurement assembly by the subject into an output load, the output load comprising at least one vertical force quantity and at least one shear force quantity, the data processing device being further configured to compute the center of gravity for the subject as a function of the at least one vertical force quantity and the at least one shear force quantity.

In a further embodiment of this aspect of the present invention, the data processing device is further configured to compute the center of gravity for the subject as a function of a height of the subject.

In yet a further embodiment, the data processing device is further configured to compute the center of gravity for the subject as a function of a center of pressure coordinate determined using the force measurement assembly.

In accordance with yet another aspect of the present invention, there is provided a method for determining the center of gravity for a subject disposed on a force measurement assembly, which includes the steps of: providing a force measurement assembly configured to receive a subject thereon, the force measurement assembly having a surface for receiving at least one portion of the body of the subject; at least one force transducer, the at least one force transducer configured to sense one or more measured quantities and output one or more signals that are representative of a load being applied to the surface of the force measurement assembly by the subject; providing a data processing device operatively coupled to the force measurement assembly, the data processing device configured to receive the one or more signals that are representative of the load being applied to the surface of the force measurement assembly by the subject and to convert the one or more signals into an output load; positioning the subject on the surface of the force measurement assembly; sensing, by utilizing the at least one force transducer, one or more measured quantities that are representative of a load being applied to the surface of the force measurement assembly by the subject and outputting one or more signals representative thereof; converting, by using the data processing device, the one or more signals that are representative of the load being applied to the surface of the force measurement assembly by the subject into an output load, the output load comprising at least one vertical force quantity and at least one shear force quantity; and computing, by using the data processing device, the center of gravity for the subject as a function of the at least one vertical force quantity and the at least one shear force quantity.

In a further embodiment of this aspect of the present invention, the method further comprises the step of: computing, by using the data processing device, the center of gravity for the subject additionally as a function of a height of the subject.

In yet a further embodiment, the method further comprises the step of: computing, by using the data processing device, the center of gravity for the subject additionally as a function of a center of pressure coordinate determined using the force measurement assembly.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 26 is a diagrammatic bottom view of a dual force plate assembly of a dual force plate system according to another exemplary embodiment of the invention illustrating the manner in which shear forces acting on the plate are determined;

FIG. 27A is a free body diagram of the left half of the beam in FIG. 28A that diagrammatically represents the shear force(s) and moment(s) acting on the left portion of the dual force plate assembly according to another exemplary embodiment of the invention;

FIG. 27B is a free body diagram of the right half of the beam in FIG. 28A that diagrammatically represents the shear force(s) and moment(s) acting on the right portion of the dual force plate assembly according to another exemplary embodiment of the invention;

Throughout the figures, the same parts are always denoted using the same reference characters so that, as a general rule, they will only be described once.

DETAILED DESCRIPTION OF EMBODIMENTS OF THE INVENTION

A. First Embodiment

Figure 1:
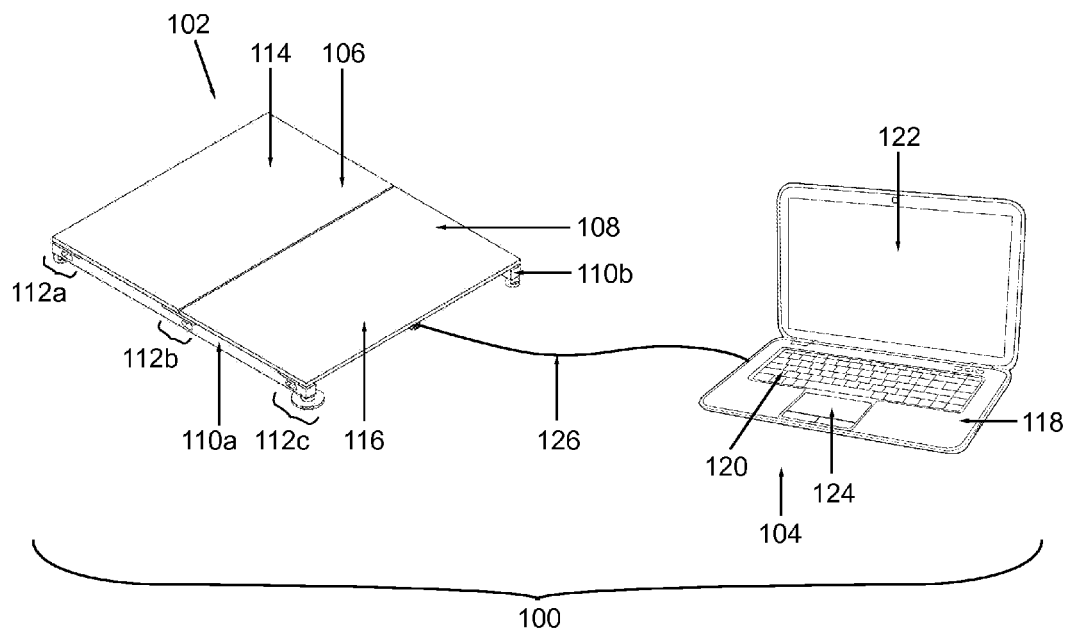
FIG. 1 is a perspective view of a dual force plate system according to a first embodiment of the invention.

A first embodiment of a dual force plate system is seen generally at 100 in FIG. 1. The dual force plate system 100 generally comprises a dual force plate assembly 102 operatively coupled to a data acquisition/data processing device 104 (i.e., a data acquisition and processing device) by virtue of an electrical cable 126. In the first embodiment, the dual force plate assembly 102 for receiving a subject utilizes a continuous force transducer beam design. In a preferred embodiment of the invention, the electrical cable 126 is used for data transmission, as well as for providing power to the dual force plate assembly 102. Preferably, the electrical cable 126 contains a plurality of electrical wires bundled together, with at least one wire being used for power and at least another wire being used for transmitting data. The bundling of the power and data transmission wires into a single electrical cable 126 advantageously creates a simpler and more efficient design. In addition, it enhances the safety of the testing environment when human subjects are being tested on the dual force plate assembly 102. However, it is to be understood that the dual force plate assembly 102 can be operatively coupled to the data acquisition/data processing device 104 using other signal transmission means, such as a wireless data transmission system. If a wireless data transmission system is employed, it is preferable to provide the dual force plate assembly 102 with a separate power supply in the form of an internal power supply or a dedicated external power supply.

Referring again to FIG. 1, it can be seen that the dual force plate assembly 102 according to the first embodiment of the invention, includes a first plate component 106, a second plate component 108, and continuous force transducer beams 110*a*, 110*b* mounted on opposite lateral sides of the first plate component 106 and second plate component 108. As depicted in FIG. 1, the continuous force transducer beams 110*a*, 110*b* extend substantially the combined width of the first plate component 106 and second plate component 108. Each continuous force transducer beam 110*a*, 110*b* includes a plurality of force transducer elements 112*a*, 112*b*, 112*c* disposed along the length thereof. The first plate component 106 has a top surface 114 that is configured to receive a first portion of a body of a subject. Similarly, the second plate component 108 has a top surface 116 that is configured to receive a second portion of a body of a subject. In a preferred embodiment, a subject stands in an upright position on the dual force plate assembly 102 and each foot of the subject is placed on the top surfaces 114, 116 of a respective plate component 106, 108 (i.e., one foot on the top surface 114 of the first plate component 106 and the other foot on the top surface 116 of the second plate component 108).

As shown in FIG. 1, the data acquisition/data processing device 104 (e.g., in the form of a laptop digital computer) generally includes a base portion 118 with a central processing unit (CPU) disposed therein for collecting and processing the data that is received from the dual force plate assembly 102, and a plurality of devices 120-124 operatively coupled to the central processing unit (CPU) in the base portion 118. Preferably, the devices that are operatively coupled to the central processing unit (CPU) comprise user input devices 120, 124 in the form of a keyboard 120 and a touchpad 124, as well as a graphical user interface in the form of a laptop LCD screen 122. While a laptop type computing system is depicted in FIG. 1, one of ordinary skill in the art will appreciate that another type of data acquisition/data processing device 104 can be substituted for the laptop computing system such as, but not limited to, a palmtop computing device (i.e., a PDA) or a desktop type computing system having a plurality of separate, operatively coupled components (e.g., a desktop type computing system including a main housing with a central processing unit (CPU) and data storage devices, a remote monitor, a remote keyboard, and a remote mouse). In addition, rather than providing a data acquisition/data processing device 104, it is to be understood that, in other embodiments, only a data acquisition device could be provided without departing from the spirit and the scope of the claimed invention.

Figure 2:
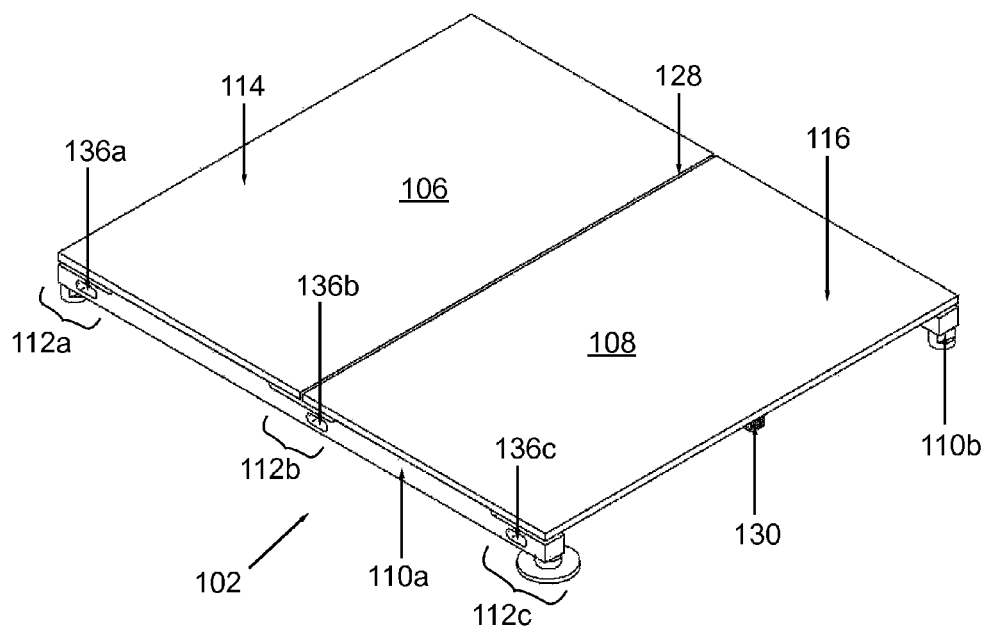
FIG. 2 is a perspective view of a dual force plate assembly of the dual force plate system according to the first embodiment of the invention.
Figure 3:
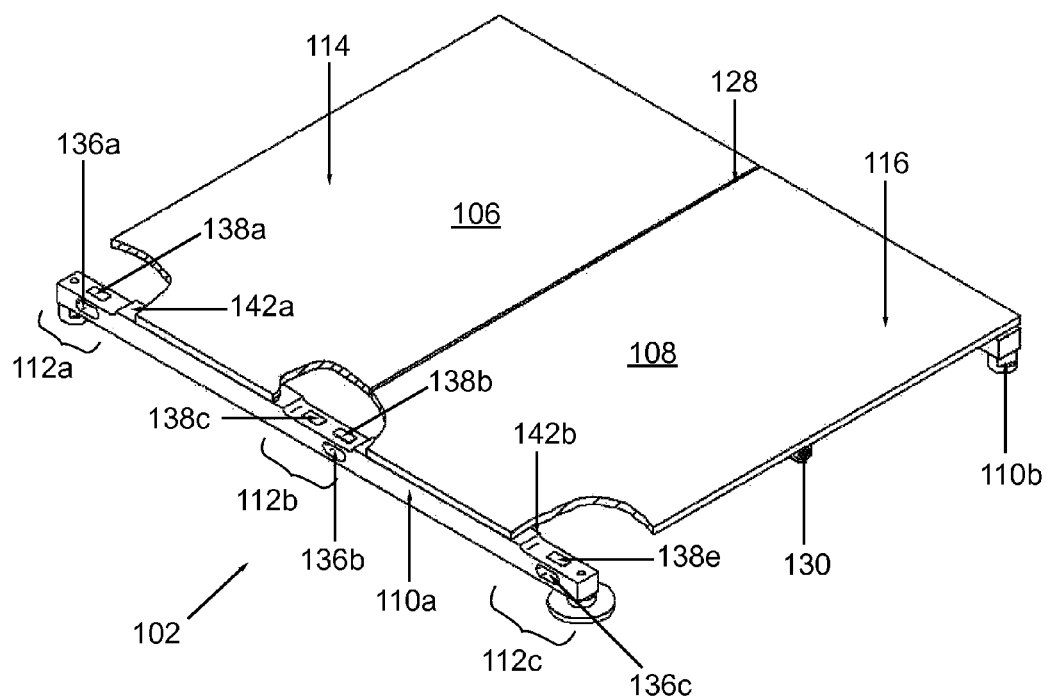
FIG. 3 is a cut-away perspective view of the dual force plate assembly of the dual force plate system according to the first embodiment of the invention.

Now, turning to FIGS. 2-4, the dual force plate assembly 102 will now be described in more detail. As described above, the dual force plate assembly 102 includes a first plate component 106 with a top surface 114 and a second plate component 108 with a top surface 116. A narrow gap 128 is provided between the first plate component 106 and the second plate component 108 so as to prevent interaction between the two plate components 106, 108. In a preferred embodiment, the narrow gap is between approximately 2 mm and approximately 3 mm, and more preferably, between 2 mm and 3 mm. As best shown in FIGS. 2 and 3, the gap 128 is continuous and completely separates the first plate component 106 from the second plate component 108 (i.e., the plate components 106, 108 do not contact one another at any location along the gap 128). In a preferred embodiment of the invention, the first and second plate components 106, 108 have a composite structure that includes an inverted top tray, structural steel members disposed inside the tray, and a metallic bottom sheet (e.g., an aluminum sheet). Alternatively, the first and second plate components 106, 108 could be provided with a composite structure that utilizes an aluminum honeycomb core inside the inverted top tray, rather than the structural steel members. In this variant of the invention, the honeycomb core is secured to the top tray and the bottom aluminum sheet using a metallic adhesive. This design allows the surface to be very stiff without adding excessive weight. In another variant of the invention, the first and second plate components 106, 108 are formed from a solid plate of material (e.g., a solid aluminum plate or a solid steel plate) with a high stiffness value. Regardless of the precise manner in which the first and second plate components 106, 108 are formed, it is highly desirable for the plate components 106, 108 to have a high stiffness value so as to ensure the structural integrity of the dual force plate assembly 102 when a subject having a substantial weight is disposed thereon. In an exemplary embodiment, the dual force plate assembly 102 is designed to have a natural frequency of at least 100 Hz and is capable of withstanding a subject weight of up to 2,225 Newtons (500 lbs.).

Advantageously, in a preferred embodiment, the dual force plate system 100, which includes dual force plate assembly 102, utilizes substantially the same number of components as a single force plate used in balance assessment.

Figure 4:
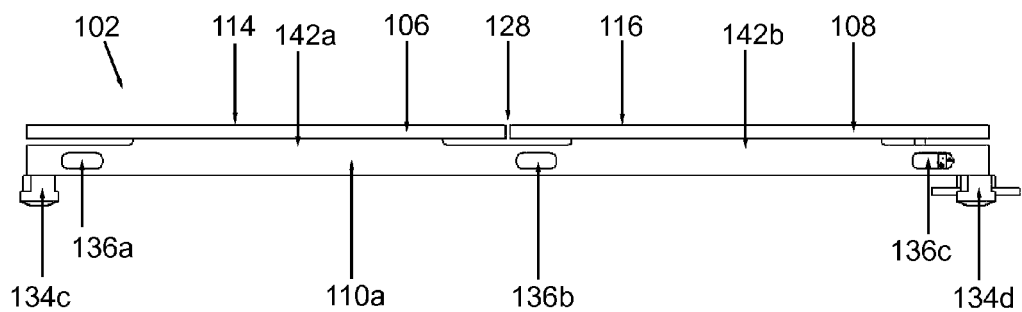
FIG. 4 is a side view of the dual force plate assembly of the dual force plate system according to the first embodiment of the invention.

Referring to FIGS. 2 and 4, it can be seen that each continuous force transducer beam 110a, 110b is attached to the underside of the first and second plate components 106, 108. In particular, as best shown in FIGS. 3 and 4, it can be seen that the top surface of each continuous force transducer beam 110a, 110b is provided with two protruding portions 142a, 142b. The protruding portions 142a, 142b are spaced apart from one another along the length of each continuous force transducer beam 110a, 110b. The top surface of the first protruding portion 142a on each of the continuous force transducer beams 110a, 110b is fixedly attached to the bottom surface of the first plate component 106, whereas the top surface of the second protruding portion 142b on each of the continuous force transducer beams 110a, 110b is fixedly attached to the bottom surface of the second plate component 108. It is highly advantageous that the first and second plate components 106, 108 only be connected to the protruding portions 142a, 142b of the continuous force transducer beams 110a, 110b so as to ensure that the total load applied to the top surfaces 114, 116 of the plate components 106, 108 is only transmitted through the force transducer elements 112a, 112b, 112c. Each force transducer beam 110a, 110b can be fixedly attached to each plate component 106, 108 by utilizing a plurality of different attachment means such as, but not limited to, threaded fasteners (e.g., screws) or different types of suitable adhesives (e.g., an adhesive designed for bonding metallic components to one another).

Figure 5:
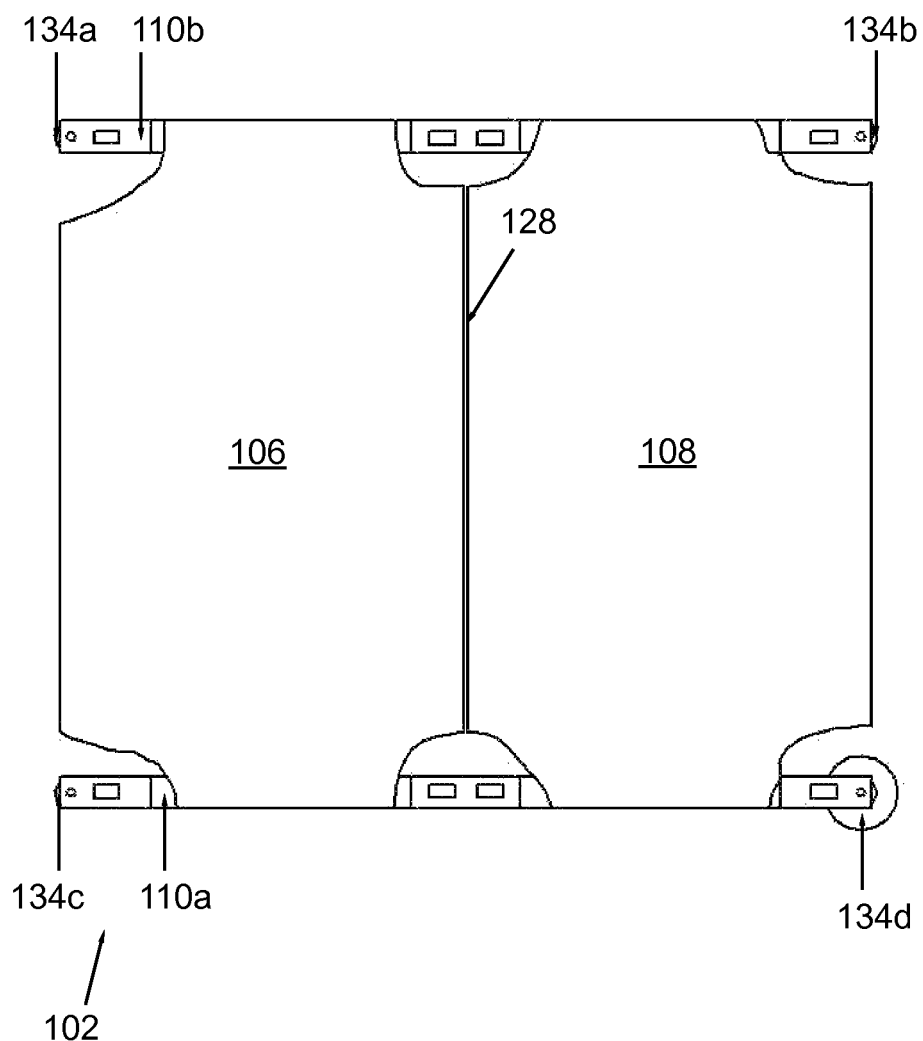
FIG. 5 is a cut-away top view of the dual force plate assembly of the dual force plate system according to the first embodiment of the invention.
Figure 6:
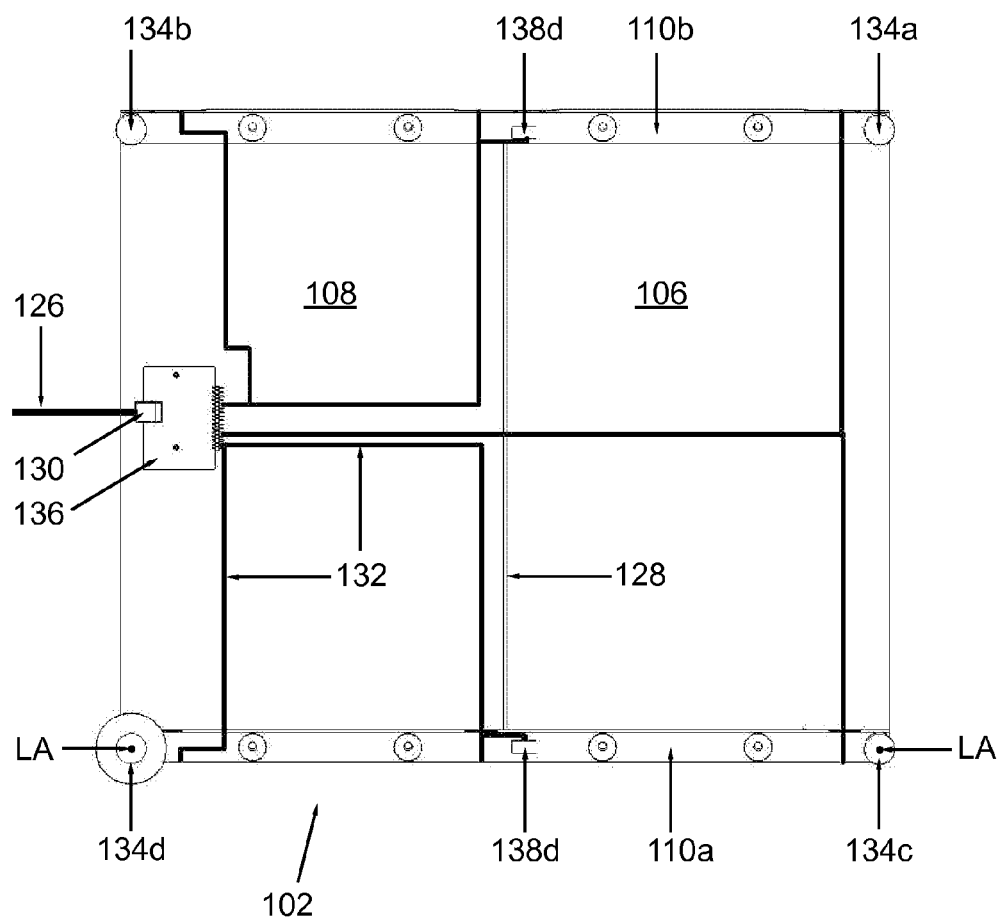
FIG. 6 is a bottom view of the dual force plate assembly of the dual force plate system according to the first embodiment of the invention.

As best illustrated in FIGS. 5 and 6, each force transducer beam 110a, 110b is provided with respective support feet 134c, 134d and 134a, 134b disposed at opposed longitudinal ends thereof. In the illustrated embodiment, the first of the two transducer beams 110a is provided with one non-adjustable support foot 134c near a first longitudinal end thereof and one adjustable support foot 134d near the other longitudinal end thereof, while the second of the two force transducer beams 110b is provided with two (2) non-adjustable support feet 134a, 134b disposed at opposed longitudinal ends thereof. The dual force plate assembly 102 is designed to be installed on a floor of a building or on any other rigid surface. The adjustable support foot 134d facilitates the leveling of the dual force plate assembly 102 on an uneven surface.

Referring again to FIGS. 5 and 6, the dual force plate assembly 102 is provided with a preamplifier board 136 mounted to the underside of the second plate component 108. As diagrammatically illustrated in FIG. 6, the preamplifier board 136 is operatively coupled to the pluralities of strain gages 138a-138e via a network of electrical wiring 132. In the depicted embodiment, the preamplifier board 136 is provided with a port 130 for receiving the end of the electrical cable 126 that operatively couples the force plate assembly 102 to the data acquisition/data processing device 104. The preamplifier board 136 is used to increase the magnitudes of the transducer analog voltages, and preferably, to convert the analog voltage signal(s) into digital voltage signal(s) as well. Advantageously, the preamplifier 136 is placed in close proximity to the two sets of force transducer elements 112a-112c in order to amplify the output voltage signal(s) before they are degraded by the effects of noise and interference while being transmitted over the substantial distance from the dual force plate assembly 102 to the data acquisition/data processing device 104. While the preamplifier board 136 is depicted as being mounted on the underside of the second plate component 108 in the illustrated embodiment of the invention, it is to be understood that, in other embodiments of the invention, the preamplifier board 136 could be alternatively mounted on the underside of the first plate component 106 or could be provided in the form of a standalone unit. Also, in yet another embodiment, an analog voltage signal(s) could be outputted from the preamplifier board 136 and then, subsequently converted to a digital voltage signal(s) at the data acquisition/data processing device 104.

In the cut-away perspective view illustrated in FIG. 3, it can be seen that the first of the two transducer beams 110a is provided with three force transducer elements 112a, 112b, 112c disposed along the length thereof. The first transducer element 112a is disposed at a first longitudinal end of the first transducer beam 110a. In a preferred embodiment of the invention, the first transducer element 112a comprises a longitudinal segment of the force transducer beam 110a, an aperture 136a disposed through the longitudinal segment of the force transducer beam 110a, and a plurality of strain gages 138a secured to the outer, top surface of the longitudinal segment of the force transducer beam 110a and substantially centered on the aperture 136a. The outer, top surface of the first transducer element 112a on which the plurality of strain gages 138a is disposed is generally opposite to the inner top surface of the aperture 136a. When a load is applied to the first plate component 106, the load is transferred to the longitudinal segment of the force transducer beam 110a that is associated with the first transducer element 112a, which operates as an elastically deformable structural member. The plurality of strain gages 138a is used to measure the deformation of the elastically deformable structural member (i.e., the longitudinal segment of the force transducer beam 110a) resulting from the vertical shear forces imparted on the member from the applied load. While in a preferred embodiment, the longitudinal segment of the force transducer beam 110a is provided with the aperture 136a therein to maximize the shear effect when the load is applied to the first plate component 106 by reducing the cross-sectional area of the beam 110a at the location of the aperture 136a, it is to be understood that the invention is not so limited. Rather, in other embodiments of the invention, the longitudinal segment of the force transducer beam 110a, which forms a component of the first transducer element 112a, is not provided with an aperture disposed therein.

As shown in FIG. 3, the second transducer element 112b is disposed in a central region of the force transducer beam 110a. In FIG. 2, it can be seen that the second force transducer element 112b extends across the gap 128 between the first plate component 106 and the second plate component 108 (i.e., the second force transducer element 112b bridges the gap 128 between the first plate component 106 and the second plate component 108). In particular, the second force transducer element 112b extends underneath the gap 128 between the first plate component 106 and the second plate component 108. Similar to the first transducer element 112a, the second transducer element 112b comprises a longitudinal segment of the force transducer beam 110a, an aperture 136b disposed through the longitudinal segment of the force transducer beam 110a, and a plurality of strain gages 138b secured to the outer, top surface of the longitudinal segment of the force transducer beam 110a and substantially centered on the aperture 136b. Also, as with the first transducer element 112a, the outer, top surface of the second transducer element 112b on which the plurality of strain gages 138b is mounted is oriented generally opposite to the inner top surface of the aperture 136b. However, unlike the first transducer element 112a, the second transducer element 112b also contains two additional pluralities of strain gages 138c, 138d mounted thereon for measuring the bending imparted on second transducer element 112b by a load applied to first plate component 106 and second plate component 108 (see FIGS. 3 and 6). The first additional plurality of strain gages 138c is mounted on the outer, top surface of the second transducer element 112b, horizontally spaced apart from the plurality of strain gages 138b. The second additional plurality of strain gages 138d is mounted on the outer, bottom surface of the second transducer element 112b, and is substantially vertically aligned with the first additional plurality of strain gages 138c (see FIG. 6). When the second transducer element 112b undergoes bending due to the application of a load on plate components 106, 108, the first additional plurality of strain gages 138c is configured to measure the deformation of the segmental portion of the force transducer beam 110a due to compression, while the second additional plurality of strain gages 138d is configured to measure the deformation of the segmental portion of the force transducer beam 110a due to tension. The shear force measurement performed by the plurality of strain gages 138b is analogous to that described above for the plurality of strain gages 138a of the first transducer element 112a. In addition, as described above for the first transducer element 112a, the aperture 136b is omitted from the second transducer element 112b in some embodiments of the invention.

Referring again to FIG. 3, it can be seen that a third transducer element 112c is disposed at a second longitudinal end of the first transducer beam 110a, which is opposite to its first longitudinal end on which the first transducer element 112a is disposed. In other words, the third transducer element 112c is generally in a mirrored relationship with respect to the first transducer element 112a. Like the first transducer element 112a, the third transducer element 112c comprises a longitudinal segment of the force transducer beam 110a, an aperture 136c disposed through the longitudinal segment of the force transducer beam 110a, and a plurality of strain gages 138e secured to the outer, top surface of the longitudinal segment of the force transducer beam 110a and substantially centered on the aperture 136c. The third transducer element 112c functions in the same manner as described above for the first transducer element 112a, except that the third transducer element 112c measures the shear force resulting from a load being applied to the second plate component 108, rather than the first plate component 106.

As shown in FIGS. 2-4, a second force transducer beam 110b is mounted on a side of the bottom surface of the first and second plate components 106, 108 that is opposite to the side of the bottom surface on which the first force transducer beam 110a is mounted. The second force transducer beam 110b is generally a mirror image of the first force transducer beam 110a. Like the first force transducer beam 110a, the second force transducer beam 110b contains first, second, and third force transducer elements 112a, 112b, 112c with respective apertures 136a, 136b, 136c disposed along the length thereof and pluralities of strain gages 138a-138e.

Figure 7:
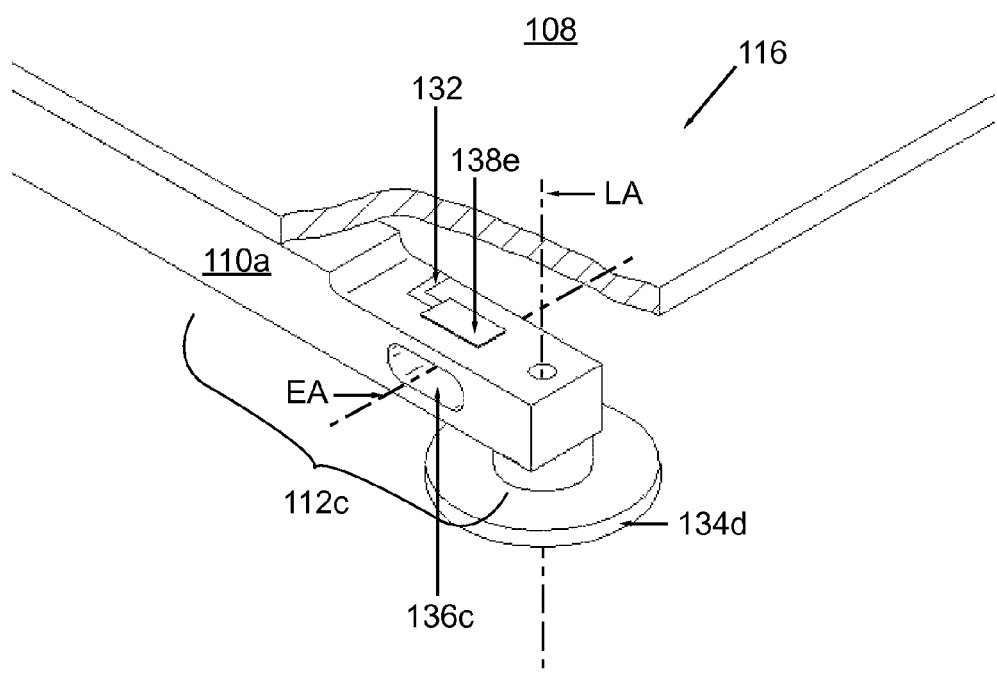
FIG. 7 is an enlarged, cut-away perspective view of a force transducer element of the dual force plate assembly according to the first embodiment of the invention, which depicts the placement of a strain gage thereon.

FIG. 7 depicts an enlarged view of force transducer element 112c. As shown in FIG. 7, the support foot 134d has a longitudinal axis LA that is disposed centrally therethrough, while the aperture 136c of the force transducer element 112c has an axis EA disposed centrally therethrough. In one or more embodiments, the structural arrangement of components illustrated in FIG. 7 is typically for each of the first and third transducer elements. The longitudinal axis LA of the support foot 134d is disposed substantially perpendicular to the extending direction of the aperture (i.e., substantially perpendicular to the axis EA). While the force transducer elements 112a, 112b, 112c shown in the drawings are beam-type force transducers, which have a generally elongated shape, one of ordinary skill in the art will appreciate that the present invention can be practiced with other types of force transducers such as, but not limited to, pylori-type force transducers. Typically, pylori-type force transducers have a plurality of strain gages adhered to the outer periphery of a cylindrically-shaped force transducer sensing element. In such a case, the force transducer elements 112a, 112c, which are disposed at opposite corners of the first and second plate components 106, 108, would be replaced with four (4) pylori-type force transducers disposed at each of the four (4) corners of the dual force plate assembly 102 (i.e., one (1) at each of the outer two corners of first plate component 106 and one (1) at each of the outer two corners of second plate component 108). In such an alternative arrangement, two force transducer elements, which are similar to force transducer elements 112b, would still be required for measuring the load transferred between the first plate component 106 and the second plate component 108.

Figure 8:
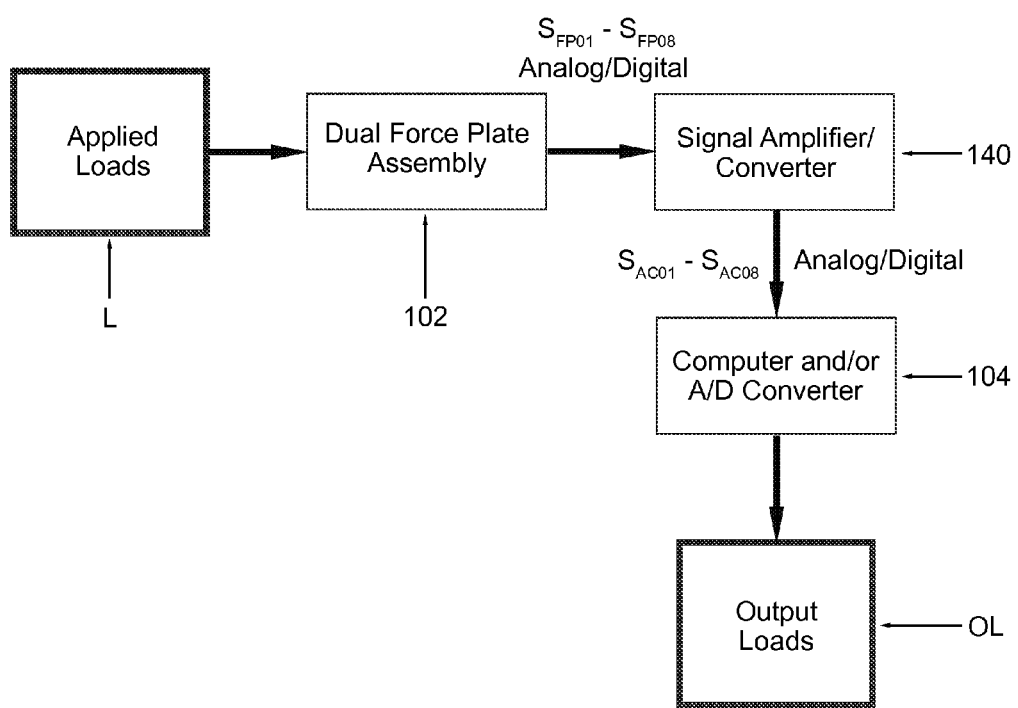
FIG. 8 is a block diagram illustrating a data acquisition/data processing system utilized in the embodiments of the force plate systems described herein.

FIG. 8 graphically illustrates the acquisition and processing of the load data carried out by the dual force plate system 100. Initially, as shown in FIG. 8, a load L is applied to the dual force plate assembly 102 by a subject disposed thereon. The load is transmitted from the first and second plate components 106, 108 to the two sets of force transducer elements 112a-112c. In a preferred embodiment of the invention, each of the force transducer elements 112a, 112c includes a plurality of strain gages wired in a Wheatstone bridge configuration, wherein the electrical resistance of each strain gage is altered when the associated longitudinal segment of the associated force transducer beam 110a, 110b undergoes deformation resulting from the load (i.e., forces and/or moments) acting on the first and second plate components 106, 108. In a preferred embodiment, the centrally-disposed force transducer elements 112b each include two (2) pluralities of strain gages wired in a Wheatstone bridge configuration, one for measuring shear and the other for measuring bending. Alternatively, rather than measuring both the shear force and bending moment, each centrally disposed transducer element 112b can measure a first bending moment at a first location along the length of the transducer element 112b and a second bending moment at a second location along the length of the transducer element 112b, the first location being spaced apart from the second location. For each plurality of strain gages disposed on the force transducer elements 112a-112c, the change in the electrical resistance of the strain gages brings about a consequential change in the output voltage of the Wheatstone bridge (i.e., a quantity representative of the load being applied to the measurement surface). Thus, the two sets of outer force transducer elements 112a, 112c transmit a total of four (4) analog output voltages (signals) to the preamplifier board 136, and the two centrally-disposed force transducer elements 112b also transmit a total of four (4) analog output voltages (signals) to the preamplifier board 136. As described above, the preamplifier board 136 is used to increase the magnitudes of the transducer analog voltages, and preferably, to convert the analog voltage signals into digital voltage signals as well. After which, the dual force plate assembly 102 transmits the force plate output signals $S_{FPO1}$-$S_{FPO8}$ to a main signal amplifier/converter 140. Depending on whether the preamplifier board 136 also includes an analog-to-digital (A/D) converter, the force plate output signals $S_{FPO1}$-$S_{FPO8}$ could be either in the form of analog signals or digital signals. The main signal amplifier/converter 140 further magnifies the force plate output signals $S_{FPO1}$-$S_{FPO8}$, and if the signals $S_{FPO1}$-$S_{FPO8}$ are of the analog-type (for a case where the preamplifier board 136 did not include an analog-to-digital (A/D) converter), it may also convert the analog signals to digital signals. Then, the signal amplifier/converter 140 transmits either the digital or analog signals $S_{ACO1}$-$S_{ACO8}$ to the data acquisition/data processing device 104 so that the forces and/or moments that are being applied to the surfaces of the dual force plate assembly 102 can be outputted to a user (i.e., the output load OL). In addition to a computer, which generally includes a central processing unit (CPU) in a base portion 118, a graphical user interface 122, and a plurality of user input devices 120, 124, the data acquisition/data processing device 104 may further comprise an analog-to-digital (A/D) converter if the signals $S_{ACO1}$-$S_{ACO8}$ are in the form of analog signals. In such a case, the analog-to-digital converter will convert the analog signals into digital signals for processing by a central processing unit (CPU).

When the data acquisition/data processing device 104 receives the voltage signals $S_{ACO1}$-$S_{ACO8}$, it transforms the signals into output forces and/or moments by multiplying the voltage signals $S_{ACO1}$-$S_{ACO8}$ by a calibration matrix. After which, the force $F_L$ exerted on the surface of the first force plate by the left foot of the subject, the force $F_R$ exerted on the surface of the second force plate by the right foot of the subject, and the center of pressure for each foot of the subject (i.e., the x and y coordinates of the point of application of the force applied to the measurement surface by each foot) are determined by the data acquisition/data processing device 104. The computations performed in the determination of the forces and center of pressure are described hereinafter.

While, in a preferred embodiment of the invention, the data acquisition/data processing device 104 determines the forces $F_L$, $F_R$ exerted on the surface of the first and second force plates by the feet of the subject and the center of pressure for each foot of the subject, it is to be understood that the invention is not so limited. Rather, in other embodiments of the invention, the output forces of the data acquisition/data processing device 104 could include all three (3) orthogonal components of the resultant forces acting on the two plate components 106, 108. In yet other embodiments of the invention, the output forces and moments of the data acquisition/data processing device 104 can be in the form of other forces and moments as well.

B. Second Embodiment

Figure 9:
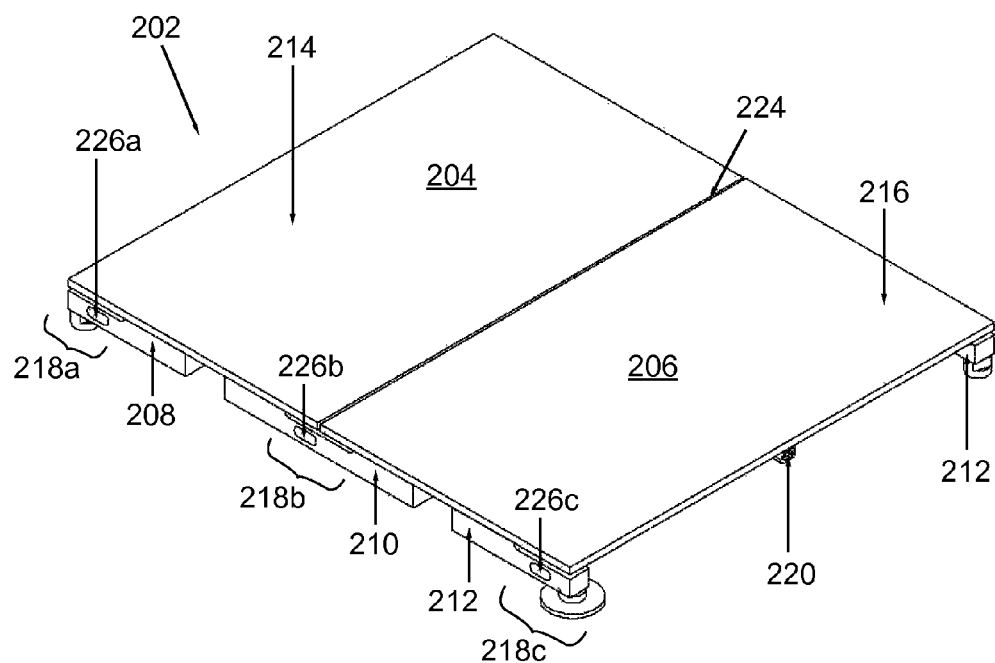
FIG. 9 is a perspective view of a dual force plate assembly of the dual force plate system according to a second embodiment of the invention.
Figure 10:
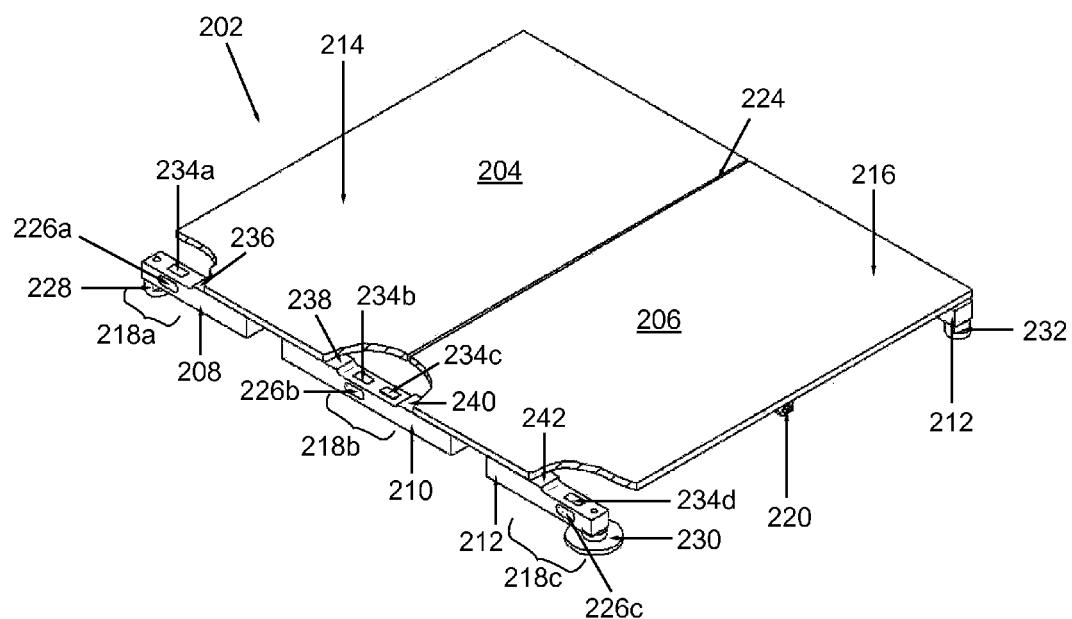
FIG. 10 is a cut-away perspective view of the dual force plate assembly of the dual force plate system according to the second embodiment of the invention.
Figure 11:
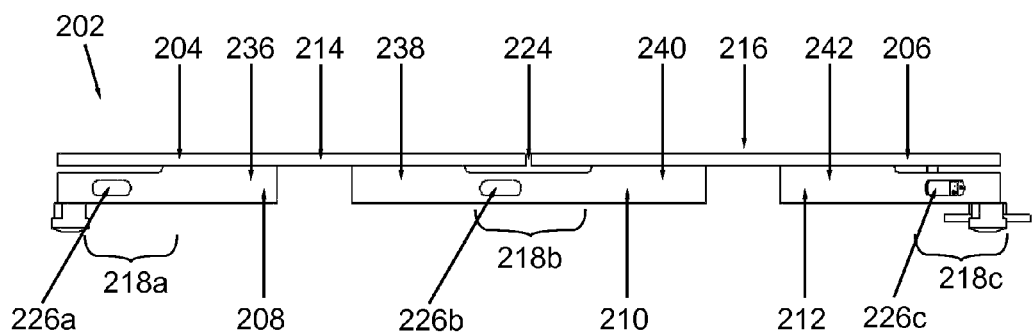
FIG. 11 is a side view of the dual force plate assembly of the dual force plate system according to the second embodiment of the invention.

A second embodiment of the dual force plate assembly is seen generally at 202 in FIG. 9, and in FIGS. 10 and 11. In accordance with the second embodiment of the invention, a dual force plate system generally comprises the dual force plate assembly 202 of FIG. 9 operatively coupled to a data acquisition/data processing device 104 by virtue of an electrical cable 126 (as illustrated in FIG. 1 for the dual force plate assembly 102). In the second embodiment, the dual force plate assembly 202 for receiving a subject utilizes a plurality of spaced apart, short transducer beams 208, 210, 212 disposed underneath, and near opposite lateral sides of, a first plate component 204 and a second plate component 206. Because the data acquisition/data processing device 104 and the electrical cable 126 are the same as that described above with regard to the first embodiment, a description of these components 104, 126 will not be repeated for this embodiment. Like the dual force plate assembly 102 of the first embodiment, the dual force plate assembly 202 also includes a preamplifier board (not explicitly shown in FIG. 9) mounted to the underside of the second plate component 206. In addition, similar to the preceding embodiment, the preamplifier board is provided with a port 220 for receiving the end of the electrical cable 126 that operatively couples the force plate assembly 202 to the data acquisition/data processing device 104.

Advantageously, the use of three discrete transducer beams 208, 210, 212 on each side of the dual force plate assembly 202, rather than two continuous beams on each side thereof, reduces the overall amount of stock materials that are required in the fabrication of the plate assembly 202. This is particularly important for dual force plate assemblies that have a large footprint.

As illustrated in FIG. 9, the dual force plate assembly 202 according to the second embodiment of the invention includes a first plate component 204, a second plate component 206, and two sets of spaced apart, short transducer beams 208, 210, 212 disposed underneath, and near opposite lateral sides of, the first plate component 204 and second plate component 206. As depicted in FIG. 9, the first short transducer beam 208 is disposed in a first corner of the dual force plate assembly 202 and includes a first force transducer element 218a. The second short transducer beam 210 is connected to both the first plate component 204 and the second plate component 206 and comprises a second force transducer element 218b, while the third short transducer beam 212 is disposed in a second corner of the dual force plate assembly 202 and includes a third force transducer element 218c. As in the first embodiment, the first plate component 204 has a top surface 214 that is configured to receive a first portion of a body of a subject. Similarly, the second plate component 206 has a top surface 216 that is configured to receive a second portion of a body of a subject. Also, similar to the first embodiment described above, a narrow gap 224 is provided between the first plate component 204 and the second plate component 206 so as to prevent interaction between the two plate components 204, 206.

Because the short transducer beams 208, 210, 212 disposed underneath, and near opposite lateral sides of, the first plate component 204 and second plate component 206 are structurally identical to one another, only one set of force transducer beams 208, 210, 212 will be described with regard to the second embodiment. As depicted in FIGS. 10 and 11, each short transducer beam 208 has a top protruding portion 236 that is fixedly attached to the bottom surface of the first plate component 204. Similarly, each oppositely disposed, short transducer beam 212 has a top protruding portion 242 that is fixedly attached to the bottom surface of the second plate component 206. Each centrally disposed short transducer beam 210, each of which extends below the gap 224, comprises a first protruding portion 238 that is fixedly attached to the bottom surface of the first plate component 204 and a second protruding portion 240 that is fixedly attached to the bottom surface of the second plate component 206. Similar to the first embodiment described above, the short transducer beams 208, 210, 212 comprise respective transducer elements 218a, 218b, 218c (which are formed by respective longitudinal segments of the force transducer beams 208, 210, 212) and respective apertures 226a, 226b, 226c disposed therethrough. Also, as in the first embodiment, the outer transducer elements 218a, 218c measure the vertical shear forces exerted on the first and second plate components 204, 206, respectively, whereas the centrally disposed transducer elements 218b measure both the vertical shear force and bending moment resulting from a load being applied to the first and second plate components 204, 206. Alternatively, rather than measuring both the vertical shear force and bending moment, each centrally disposed transducer element 218b can measure a first bending moment at a first location along the length of the transducer element 218b and a second bending moment at a second location along the length of the transducer element 218b, the first location being spaced apart from the second location.

Like the force transducer element 112a described with regard to the first embodiment of the invention, the force transducer element 218a is provided with a plurality of strain gages 234a secured to the outer, top surface of the longitudinal segment of the force transducer beam 208 and substantially centered on the aperture 226a (see FIG. 10). Also, similar to the force transducer element 112c of the first embodiment, the force transducer element 218c is provided with a plurality of strain gages 234d secured to the outer, top surface of the longitudinal segment of the force transducer beam 212 and substantially centered on the aperture 226c. In addition, like the force transducer element 112b of the first embodiment of the invention, the force transducer element 218b is provided with a plurality of strain gages 234b secured to the outer, top surface of the longitudinal segment of the force transducer beam 210 and substantially centered on the aperture 226b, a first additional plurality of strain gages 234c mounted on the outer, top surface of the second transducer element 218b, horizontally spaced apart from the plurality of strain gages 234b, and a second additional plurality of strain gages (not shown) mounted on the outer, bottom surface of the second transducer element 218b, and substantially vertically aligned with the first additional plurality of strain gages 234c.

As explained above with regard to the first embodiment of the invention, it is highly advantageous that the first and second plate components 204, 206 only be connected to the protruding portions 236, 238, 240, 242 of the short force transducer beams 208, 210, 212 so as to ensure that the total load applied to the top surfaces 214, 216 of the plate components 204, 206 is only transmitted through the force transducer elements 218a, 218b, 218c of the force transducer beams 208, 210, 212.

In the second embodiment of the invention, each short force transducer beam 208, 212 is provided with a respective support foot disposed near an outer end thereof. In FIG. 10, it can be seen that the first of the two short force transducer beams 208 is provided with one non-adjustable support foot 228 near the outer end thereof, whereas the first of the two short force transducer beams 212 is provided with one adjustable support foot 230 near the outer end thereof. Also, as depicted in FIG. 10, the second of the two short force transducer beams 212 is provided with a non-adjustable support foot 232, which is substantially the same as non-adjustable support foot 228. The second of the two force transducer beams 208 is not explicitly shown in FIG. 10, but it is provided with a non-adjustable support foot disposed near an outer end thereof, which is generally the same as non-adjustable support feet 228, 232. Like the dual force plate assembly 102 in the first embodiment of the invention, the dual force plate assembly 202 is designed to be installed on a floor of a building or on any other rigid surface. The adjustable support foot 230 facilitates the leveling of the dual force plate assembly 202 on an uneven surface.

C. Third Embodiment

Figure 12:
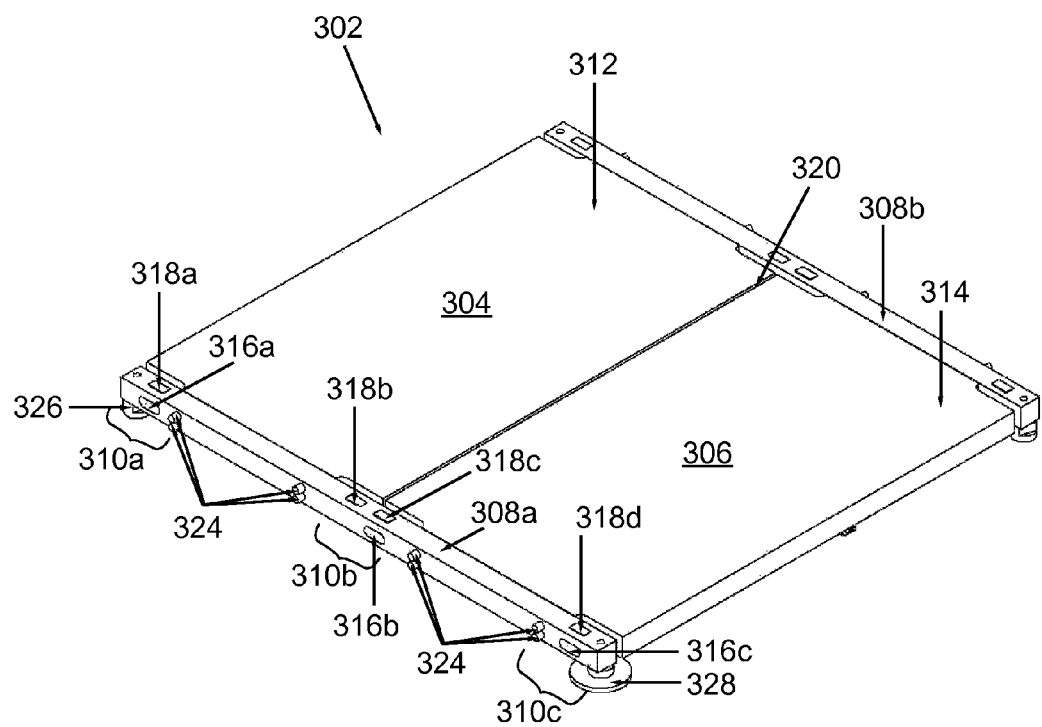
FIG. 12 is a perspective view of a dual force plate assembly of the dual force plate system according to a third embodiment of the invention.
Figure 13:
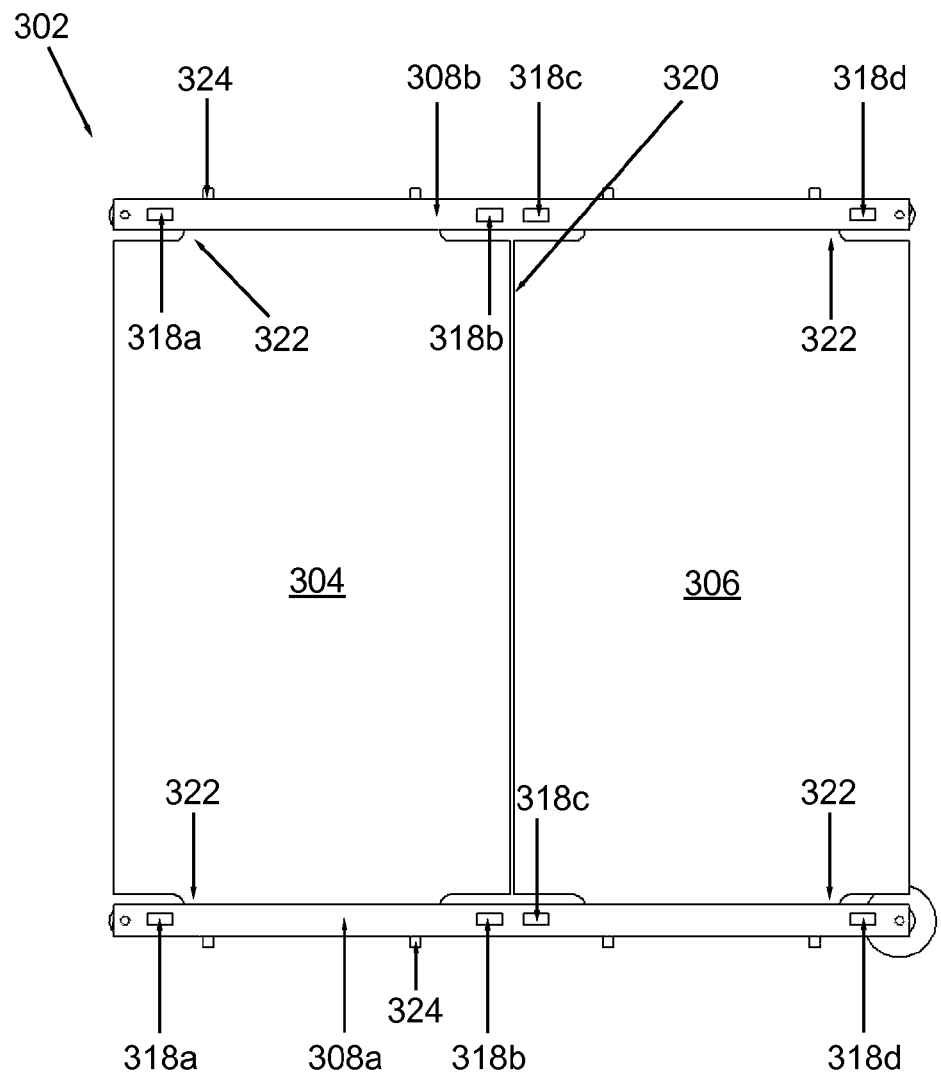
FIG. 13 is a top view of the dual force plate assembly of the dual force plate system according to the third embodiment of the invention.

A third embodiment of the dual force plate assembly is seen generally at 302 in FIGS. 12 and 13. In accordance with the third embodiment of the invention, the dual force plate assembly 302 for receiving a subject utilizes continuous force transducer beams 308*a*, 308*b* disposed on opposite lateral sides of the first and second plate components 304, 306, rather than force transducer beams disposed underneath the first and second plate components as described with regard to the first and second embodiments of the invention. As explained above in conjunction with the preceding two embodiments, the first plate component 304 has a top surface 312 that is configured to receive a first portion of a body of a subject. Similarly, the second plate component 306 has a top surface 314 that is configured to receive a second portion of a body of a subject. Also, similar to the first two embodiments described above, a continuous narrow gap 320 is provided between the first plate component 304 and the second plate component 306 so as to prevent interaction between the two plate components 304, 306.

Advantageously, in a preferred embodiment, the dual force plate assembly 302 has an overall height that is significantly lower than conventional force plates used in balance assessment. This reduction in height is made possible, in part, by the mounting of the continuous force transducer beams 308*a*, 308*b* on the lateral sides of the first and second plate components 304, 306.

Referring to FIG. 12, it can be seen that each continuous force transducer beam 308*a*, 308*b* includes a plurality of force transducer elements 310*a*, 310*b*, 310*c* disposed along the length thereof. Also, similar to the preceding two embodiments of the invention, each of the plurality of force transducer elements 310*a*, 310*b*, 310*c* is provided with a respective aperture 316*a*, 316*b*, 316*c* disposed therethrough. Moreover, as in the preceding embodiments, the outer transducer elements 310*a*, 310*c* measure the vertical shear forces exerted on the first and second plate components 304, 306, respectively, whereas the centrally disposed transducer elements 310*b* measure both the vertical shear force and bending moment resulting from a load being applied to the first and second plate components 304, 306. Alternatively, rather than measuring both the vertical shear force and bending moment, each centrally disposed transducer element 310*b* can measure a first bending moment at a first location along the length of the transducer element 310*b* and a second bending moment at a second location along the length of the transducer element 310*b*, the first location being spaced apart from the second location.

Like the force transducer elements 112*a*, 218*a* described with regard to the first two embodiments of the invention, each first force transducer element 310*a* is provided with a plurality of strain gages 318*a* secured to the outer, top surface of its associated force transducer beam 308*a*, 308*b*, and substantially centered on the aperture 316*a* (see FIG. 12). Also, similar to the force transducer elements 112*c*, 218*c* of the first two embodiments, each force transducer element 310*c* is provided with a plurality of strain gages 318*d* secured to the outer, top surface of its associated force transducer beam 308*a*, 308*b*, and substantially centered on the aperture 316*c*. In addition, like the force transducer elements 112*b*, 218*b* of the first two embodiments of the invention, each force transducer element 310*b* is provided with a plurality of strain gages 318*c* secured to the outer, top surface of its associated force transducer beam 308*a*, 308*b* and substantially centered on the aperture 316*b*, a first additional plurality of strain gages 318*b* mounted on the outer, top surface of the second transducer element 310*b*, horizontally spaced apart from the plurality of strain gages 318*c*, and a second additional plurality of strain gages (not shown) mounted on the outer, bottom surface of the second transducer element 310*b*, and substantially vertically aligned with the first additional plurality of strain gages 318*b*. In FIG. 12, it can be seen that the second force transducer element 310*b* extends across the gap 320 between the first plate component 304 and the second plate component 306 (i.e., the second force transducer element 310*b* bridges the gap 320 between the first plate component 304 and the second plate component 306).

Referring to FIGS. 12 and 13, it can be seen that each continuous force transducer beam 308*a*, 308*b* is fixedly attached to adjacent lateral sides of the first and second plate components 304, 306 using a plurality of screws 324. In particular, as best shown in the top view of FIG. 13, each force transducer beam 308*a*, 308*b* is attached to a respective centrally disposed protruding portion 322 on opposite lateral sides of the first plate component 304 and the second plate component 306. It is highly advantageous that the force transducer beams 308*a*, 308*b* only be connected to the centrally disposed protruding portions 322 of the first and second plate component 304, 306 so as to ensure that the total load applied to the top surfaces 312, 314 of the plate components 304, 306 is only transmitted through the force transducer elements 310*a*, 310*b*, 310*c* on each side thereof. In FIG. 12, a total of four (4) screws 324 are used to connect each force transducer beam 308*a*, 308*b* to each plate component 304, 306. However, it is to be understood that the invention is not so limited. Rather, in other embodiments of the invention, more than four screws or less than four screws could be used to fixedly attach each force transducer beam 308*a*, 308*b* to each force plate component 304, 306. In yet other embodiments of the invention, the force transducer beams 308*a*, 308*b* could be connected to plate components 304, 306 by using different types of suitable adhesives (e.g., an adhesive designed for bonding metallic components to one another).

As best depicted in FIG. 12, the top surface 312 of the first plate component 304 and the top surface 314 of the second plate component 306 are both substantially aligned with the top surfaces of the transducer beams 308*a*, 308*b* (i.e., they are substantially flush with the top surfaces of the transducer beams 308*a*, 308*b*) in a preferred embodiment of the invention. This design feature enables the profile of the dual force plate assembly 302 to be minimized so that subjects are able to easily step on and off the dual force plate assembly 302. Also, it prevents the transducer beams 308*a*, 308*b* from posing a tripping hazard to subjects, as would be the case if the top surfaces of the transducer beams 308*a*, 308*b* were disposed above the top surfaces 312, 314 of the first and second plate components 304, 306. However, it is to be understood that the invention is not so limited. For example, in other embodiments of the invention, the top surfaces of the transducer beams 308*a*, 308*b* could be disposed below the top surfaces 312, 314 of the first and second plate components 304, 306.

In the third embodiment of the invention, each force transducer beam 308*a*, 308*b* is provided with respective support feet disposed at opposed longitudinal ends thereof. In FIG. 12, it can be seen that the first of the two transducer beams 308*a* is provided with one non-adjustable support foot 326 near a first longitudinal end thereof and one adjustable support foot 328 near the other longitudinal end thereof. The bottom portion of the second of the two force transducer beams 308*b* is not explicitly shown in FIG. 12, but it is provided with two (2) non-adjustable support feet disposed at opposed longitudinal ends thereof, both of which are generally the same as non-adjustable support foot 326. The dual force plate assembly 302 is designed to be installed on a floor of a building or on any other rigid surface. The adjustable support foot 328 facilitates the leveling of the dual force plate assembly 302 on an uneven surface.

D. Fourth Embodiment

Figure 14:
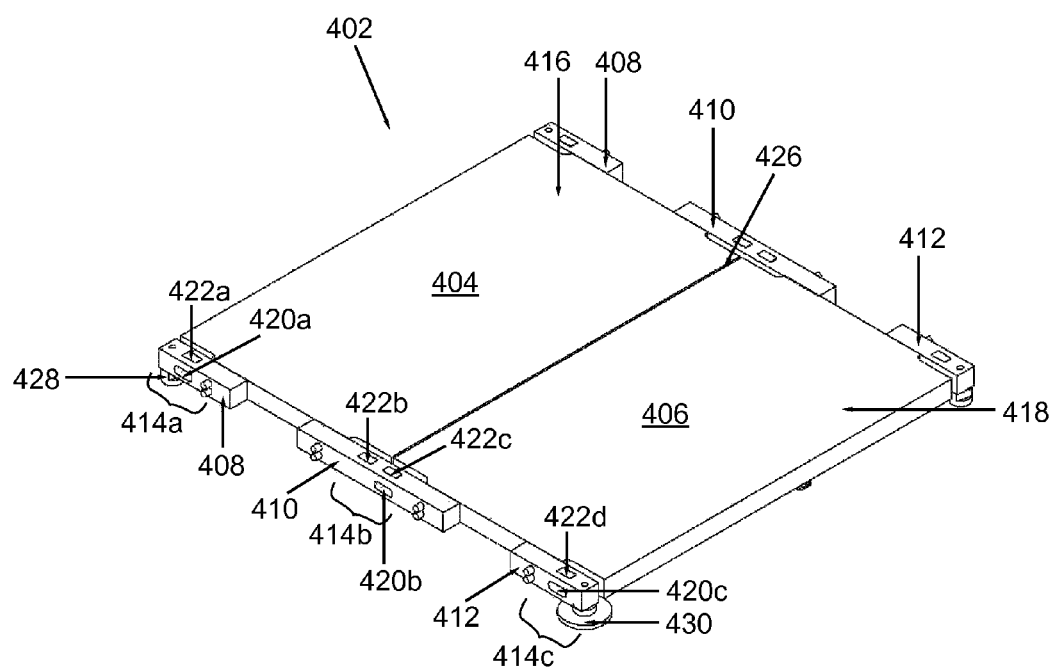
FIG. 14 is a perspective view of a dual force plate assembly of the dual force plate system according to a fourth embodiment of the invention.
Figure 15:
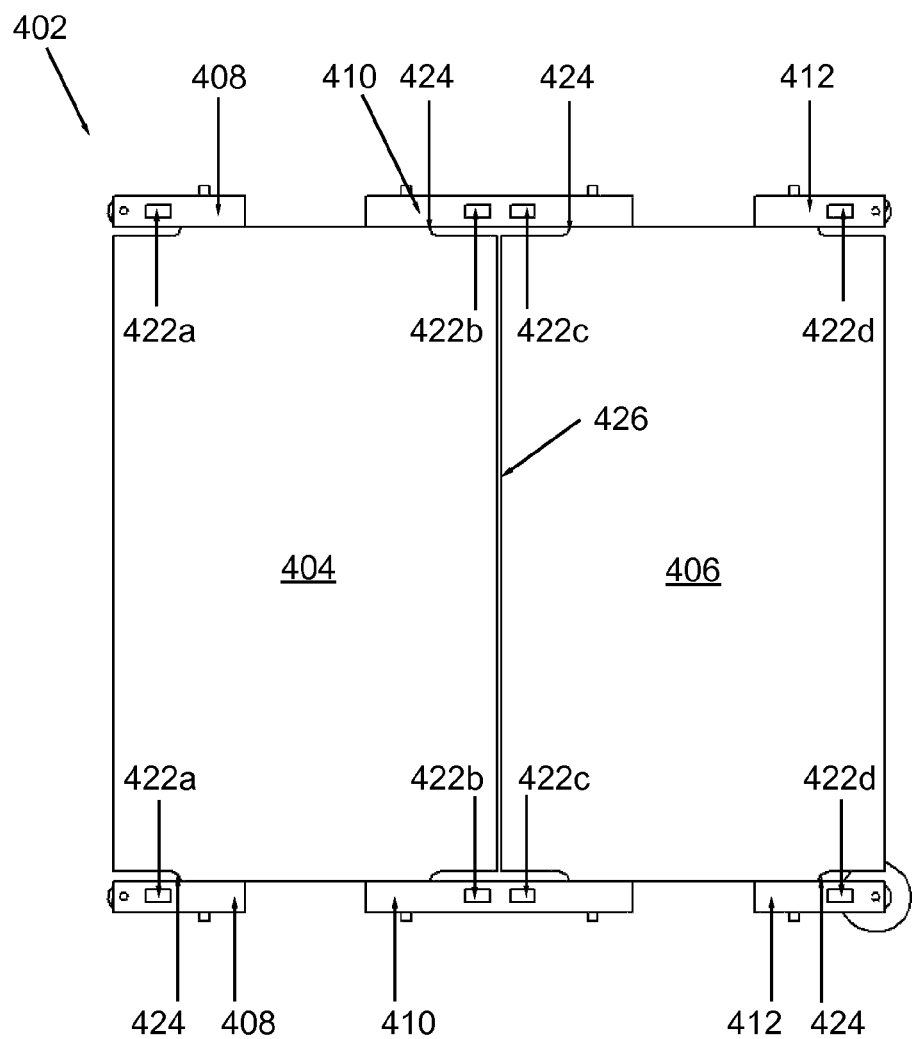
FIG. 15 is a top view of the dual force plate assembly of the dual force plate system according to the fourth embodiment of the invention.

A fourth embodiment of the dual force plate assembly is seen generally at 402 in FIGS. 14 and 15. In accordance with the fourth embodiment of the invention, the dual force plate assembly 402 for receiving a subject utilizes two sets of spaced apart, short transducer beams 408, 410, 412 disposed on opposite lateral sides of first and second plate components 404, 406, rather than the continuous transducer beams 308a, 308b described with respect to the third embodiment of the invention. As explained above in conjunction with the preceding three embodiments, the first plate component 404 has a top surface 416 that is configured to receive a first portion of a body of a subject. Similarly, the second plate component 406 has a top surface 418 that is configured to receive a second portion of a body of a subject. Also, similar to the first three embodiments described above, a continuous narrow gap 426 is provided between the first plate component 404 and the second plate component 406 so as to prevent interaction between the two plate components 404, 406. Similar to the preceding embodiments described above, the short transducer beams 408, 410, 412 comprise respective transducer elements 414a, 414b, 414c (which are formed by respective longitudinal segments of the force transducer beams 408, 410, 412) and respective apertures 420a, 420b, 420c disposed therethrough. Also, as in the preceding embodiments, the outer transducer elements 414a, 414c measure the vertical shear forces exerted on the first and second plate components 404, 406, respectively, whereas the centrally disposed transducer elements 414b measure both the vertical shear force and bending moment resulting from a load being applied to the first and second plate components 404, 406. Alternatively, rather than measuring both the vertical shear force and bending moment, each centrally disposed transducer element 414b can measure a first bending moment at a first location along the length of the transducer element 414b and a second bending moment at a second location along the length of the transducer element 414b, the first location being spaced apart from the second location.

Like the force transducer elements 112a, 218a, 310a described with regard to the first three embodiments of the invention, the first force transducer element 414a is provided with a plurality of strain gages 422a secured to the outer, top surface of the force transducer beam 408 and substantially centered on the aperture 420a (see FIG. 14). Also, similar to the force transducer elements 112c, 218c, 310c of the first three embodiments, the force transducer element 414c is provided with a plurality of strain gages 422d secured to the outer, top surface of the force transducer beam 412 and substantially centered on the aperture 420c. In addition, like the force transducer elements 112b, 218b, 310b of the first three embodiments of the invention, the force transducer element 414b is provided with a plurality of strain gages 422c secured to the outer, top surface of the force transducer beam 410 and substantially centered on the aperture 420b, a first additional plurality of strain gages 422b mounted on the outer, top surface of the second transducer element 414b, horizontally spaced apart from the plurality of strain gages 422c, and a second additional plurality of strain gages (not shown) mounted on the outer, bottom surface of the second transducer element 414b, and substantially vertically aligned with the first additional plurality of strain gages 422b.

Now, referring to FIGS. 14 and 15, it can be seen that each first short transducer beam 408 is fixedly attached to the outer end portion of a respective centrally disposed protruding portion 424 on opposite lateral sides of the first plate component 404. Similarly, each third short transducer beam 412 is fixedly attached to the outer end portion of a respective centrally disposed protruding portion 424 on opposite lateral sides of the second plate component 406. Also, as depicted in FIGS. 14 and 15, each second short transducer beam 410 is fixedly attached to both the inner end portion of a respective centrally disposed protruding portion 424 on a lateral side of the first plate component 404 and the inner end portion of a respective centrally disposed protruding portion 424 on an adjacent lateral side of the second plate component 406. As described above with regard to the third embodiment, it is highly advantageous that the spaced apart, short transducer beams 408, 410, 412 only be connected to the first and second plate components 404, 406 by means of the centrally disposed protruding portions 424 so as to ensure that the total load applied to the top surfaces 416, 418 of the plate components 404, 406 is only transmitted through the force transducer elements 414a, 414b, 414c.

In the fourth embodiment of the invention, each short force transducer beam 408, 412 is provided with a respective support foot disposed near an outer end thereof. In FIG. 14, it can be seen that the first of the two short force transducer beams 408 is provided with one non-adjustable support foot 428 near the outer end thereof, whereas the first of the two short force transducer beams 412 is provided with one adjustable support foot 430 near the outer end thereof. Also, while not explicitly shown in FIG. 14, the second of the two short force transducer beams 408 is provided with a non-adjustable support foot near an outer end thereof, which is substantially the same as non-adjustable support foot 428. Also, referring to FIG. 14, the second of the two short force transducer beams 412 is provided with a non-adjustable support foot near an outer end thereof, which is generally equivalent to non-adjustable support foot 428. Like the dual force plate assemblies described in the preceding embodiments of the invention, the dual force plate assembly 402 is designed to be installed on a floor of a building or on any other rigid surface. The adjustable support foot 430 facilitates the leveling of the dual force plate assembly 402 on an uneven surface.

E. Fifth Embodiment

Figure 16:
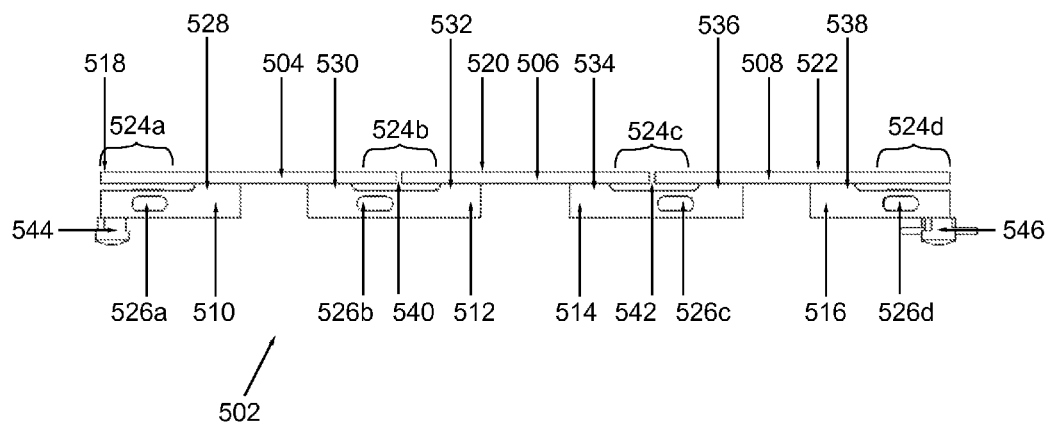
FIG. 16 is a side view of a triple force plate assembly of a triple force plate system according to a fifth embodiment of the invention.

A fifth embodiment of the dual force plate assembly is seen generally at 502 in FIG. 16. In accordance with the fifth embodiment of the invention, the dual force plate assembly 502 for receiving a subject utilizes three plate components 504, 506, 508, rather than two plate components as employed in the previous embodiments of the invention. Two sets of spaced apart, short transducer beams 510, 512, 514, 516 are disposed underneath, and near opposite sides of, the first, second, and third plate components 504, 506, 508. As depicted in FIG. 16, each short transducer beam 510 has a top protruding portion 528 that is fixedly attached to the bottom surface of the first plate component 504. Similarly, each oppositely disposed, short transducer beam 516 has a top protruding portion 538 that is fixedly attached to the bottom surface of the third plate component 508. Each short transducer beam 512, which extends below a continuous gap 540 between the first and second plate components 504, 506, comprises a first protruding portion 530 that is fixedly attached to the bottom surface of the first plate component 504 and a second protruding portion 532 that is fixedly attached to the bottom surface of the second plate component 506. Similarly, each short transducer beam 514, which extends below a continuous gap 542 between the second and third plate components 506, 508, comprises a first protruding portion 534 that is fixedly attached to the bottom surface of the second plate component 506 and a second protruding portion 536 that is fixedly attached to the bottom surface of the third plate component 508. Like the preceding embodiments described above, the short transducer beams 510, 512, 514, 516 comprise respective transducer elements 524a, 524b, 524c, 524d and respective apertures 526a, 526b, 526c, 526d disposed therethrough. Also, similar to that described with regard to the preceding embodiments, the outer transducer elements 524a, 524d measure the vertical shear forces exerted on the first and third plate components 504, 508, respectively, whereas the centrally disposed transducer elements 524b measure both the vertical shear force and bending moment resulting from a load being applied to the first and second plate components 504, 506 and the centrally disposed transducer elements 524c measure both the vertical shear force and bending moment resulting from a load being applied to the second and third plate components 506, 508. Alternatively, rather than measuring both the vertical shear force and bending moment, each centrally disposed transducer element 524b, 524c can measure a first bending moment at a first location along the length of the transducer element 524b, 524c and a second bending moment at a second location along the length of the transducer element 524b, 524c, the first location being spaced apart from the second location.

As explained above with regard to the preceding embodiments of the invention, it is highly advantageous that the first, second, and third plate components 504, 506, 508 only be connected to the protruding portions 528, 530, 532, 534, 536, 538 of the short force transducer beams 510, 512, 514, 516 so as to ensure that the total load applied to the top surfaces 518, 520, 522 of the plate components 504, 506, 508 is only transmitted through the force transducer elements 524a, 524b, 525c, 524d of the force transducer beams 510, 512, 514, 516.

In the fifth embodiment of the invention, each short force transducer beam 510 is provided with a non-adjustable support foot 544 near the outer longitudinal end thereof. One of the two short force transducer beams 516 is also provided with a non-adjustable support foot 544 near the outer longitudinal end thereof (not visible in FIG. 16), whereas the other of the two short force transducer beams 516 is provided with an adjustable support foot 546 to permit the leveling of the dual force plate assembly 502 on an uneven surface.

F. Computations Performed by the Data Acquisition/Data Processing Device 104

Now, the manner in which the data acquisition/data processing device 104 calculates the applied forces and the center of pressure for each of the subject's two feet will be described in detail. The center of pressure for each foot of the subject comprises the x and y coordinates of the point of application of the force applied to the measurement surface by that foot. During the balance assessment of a patient, the variation in the center of pressure (i.e., the sway of the patient) is monitored so as to determine the overall stability of that patient. Initially, referring to FIGS. 17A-17D, the mathematical determination of the x-coordinates for each foot of the subject will be explained. Then, with reference to FIG. 18, the determination of the y-coordinates for each foot of the subject will be described.

Figures 17A, 17B, 17C, 17D:
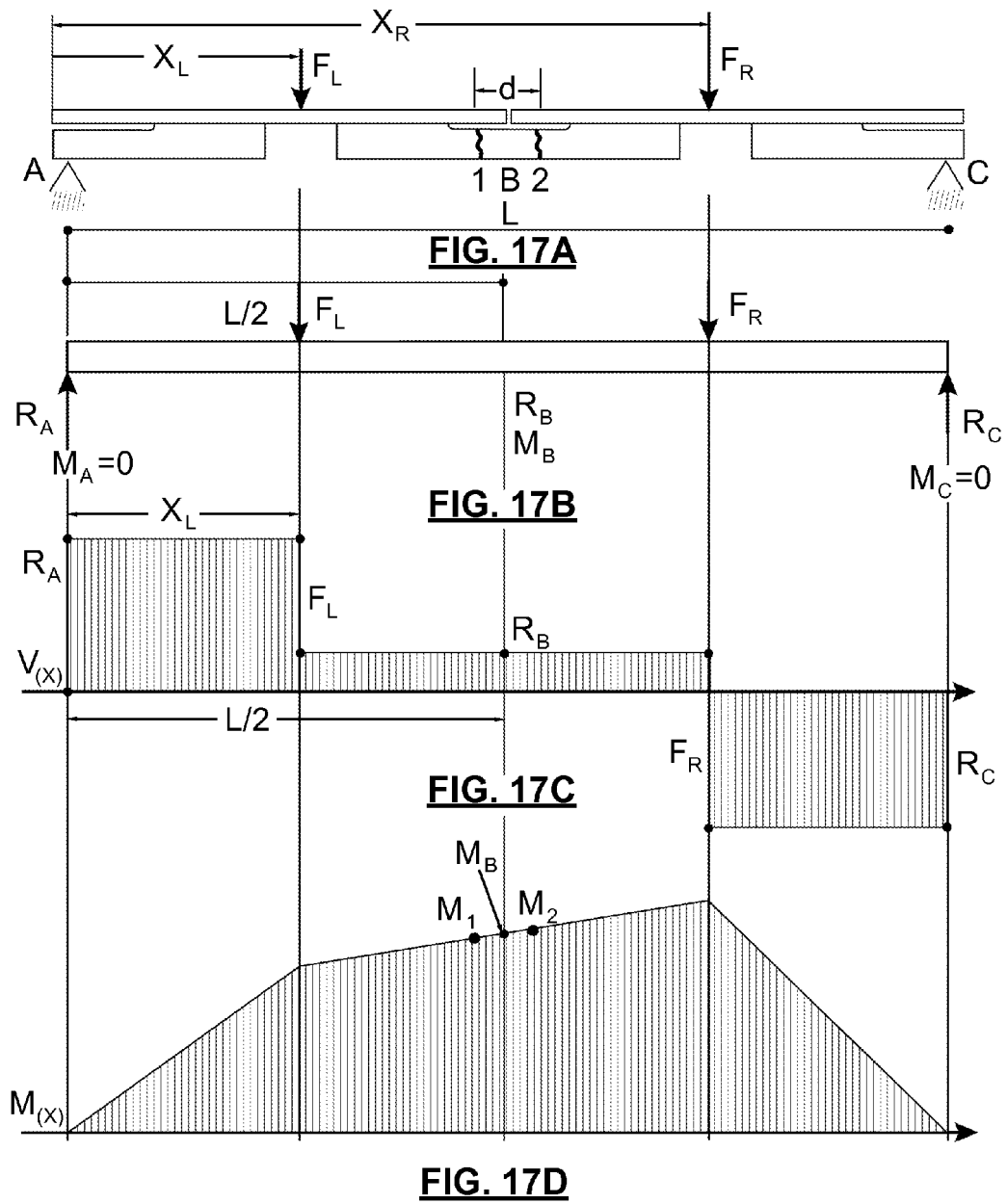
FIG. 17A is a side view of a dual force plate assembly of a dual force plate system according to an exemplary embodiment of the invention with exemplary applied forces depicted thereon so as to illustrate the manner in which the x-coordinates of the center-of-pressure are determined.
FIG. 17B is a free body diagram that diagrammatically represents the forces and moments acting on the dual force plate assembly according to an exemplary embodiment of the invention.
FIG. 17C is a shear diagram that diagrammatically represents the shear forces acting on the dual force plate assembly according to an exemplary embodiment of the invention.
FIG. 17D is a moment diagram that diagrammatically represents the moments acting on the dual force plate assembly according to an exemplary embodiment of the invention.

FIG. 17A depicts a side view of a dual force plate assembly of a dual force plate system, wherein the unknown parameters to be determined are diagrammatically depicted thereon. The first set of unknown parameters comprises: (i) the force $F_L$ applied to the first measurement surface of the first force plate by the left foot of the subject, and (ii) the force $F_R$ applied to the second measurement surface of the second force plate by the right foot of the subject. The second set of unknown parameters comprises: (i) the distance $x_L$ measured from a reference point at the outer edge of the first force plate to the point of application of the force $F_L$ exerted on the first measurement surface by the left foot of the subject, and (ii) the distance $x_R$ measured from a reference point at the outer edge of the first force plate to the point of application of the force $F_R$ exerted on the second measurement surface by the right foot of the subject (i.e., the x-coordinates of the center of pressure for each foot of the subject). Thus, initially there are a total of four unknown parameters that need to be determined.

In FIG. 17A, the dual force plate assembly is diagrammatically depicted as being supported on simple supports, which are otherwise known as knife-edge supports. This model is appropriate for the typical arrangement of the dual force plate assembly in which the feet of the assembly are simply resting on the surface of the floor, and thus, there is no moment reaction at the supports. However, it is to be understood that the invention is not so limited. Rather, in other embodiments of the invention, the feet of the dual force plate assembly are fixedly attached to the floor, and therefore, the connections between the force plate assembly and the floor are capable of transmitting moments. The mathematical analysis for such an arrangement would be similar to that provided below except that non-zero moments would be present at each support.

In FIG. 17B, a free diagram body of the dual force plate assembly is shown in order to graphically illustrate measured parameters of the system. Referring to this figure, it can be seen that the dual force plate assembly is being modeled as one continuous, simply supported beam. The dual force plate assembly can be accurately modeled as a single beam because the center transducer beams, each of which operatively connects the first plate to the second plate, are fixedly attached to the bottom surfaces of the first and second plates. Thus, even though separate components are utilized in the actual assembly, the dual force plate operates as if it is a single structure. As depicted in FIG. 17B, the shear force $R_A$ acting on the left end of the assembly is sensed by a first force transducer element, while the shear force $R_C$ acting on the right end of the assembly is measured by a second force transducer element. The third force transducer element, which is disposed on the center transducer beam, measures both the shear force $R_B$ and the moment $M_B$ (i.e., it measures the load transferred between the first and second plates).

Now that both the unknown parameters and the measured parameters of the dual force plate system have been defined, the mathematical equations for determining the unknown parameters of the system can be formulated. The forces exerted on the first and second force plates by the respective left and right feet of the subject are described by the following two equations:

$$F_L = R_A - R_R \qquad (1)$$

$$F_R = R_R + R_C \qquad (2)$$

where:
$F_L$: force exerted on the surface of the first force plate by the left foot of the subject;
$F_R$: force exerted on the surface of the second force plate by the right foot of the subject;
$R_A$: vertical force measured by the first force transducer element;

$R_B$: vertical force measured by the third force transducer element (i.e. between the two plates); and $R_C$: vertical force measured by the second force transducer element.

Thus, applied forces can be obtained by plugging the shear forces $R_A$, $R_B$, and $R_C$, which are measured by the force transducer elements, into equations (1) and (2) and then, solving for forces $F_L$ and $F_R$.

Alternatively, if each centrally disposed transducer element measures a first and second bending moment $M_1$, $M_2$, rather than the shear force and a single bending moment, then the shear force $R_B$ can be determined by utilizing the following equation:

$$R_B = \frac{(M_2 - M_1)}{d} \quad (3)$$

where:

$M_1$: first bending moment measured at a first location along the length of the third transducer element (e.g., see FIG. 17A, centrally located transducer beam);

$M_2$: second bending moment measured at a second location along the length of the third transducer element (e.g., see FIG. 17A, centrally located transducer beam); and d: distance between the first location and the second location along the length of the third transducer element (e.g., see FIG. 17A, centrally located transducer beam).

Then, the applied forces $F_L$, $F_R$ can be determined from equations (1) and (2) by using the computed shear force $R_B$ together with the measured shear forces $R_A$ and $R_C$.

Next, turning to the shear diagram depicted in FIG. 17C, the moment $M_B$ is equal to the area under the shear force curves as follows:

$$M_B = \left(R_B \cdot \left(\frac{L}{2}\right)\right) + (F_L \cdot x_L) \quad (4)$$

where:

$M_B$ moment about point B;

$R_B$: shear force measured by the third force transducer element (i.e. between the two plates) or computed;

L: overall length of the dual force plate assembly (i.e., combined length of the first and second force plates);

$F_L$: force exerted on the surface of the first force plate by the left foot of the subject; and $x_L$: distance measured from a reference point at the outer edge of the first force plate to the point of application of the force $F_L$ exerted on the first measurement surface by the left foot of the subject;

The moment $M_B$ is graphically depicted in the moment diagram of FIG. 17D. Then, in order to solve for the desired unknown quantity, the terms of equation (4) are rearranged as follows:

$$x_L = \frac{M_B - \left(R_B \cdot \left(\frac{L}{2}\right)\right)}{F_L} \quad (5)$$

Similarly, the unknown coordinate $x_R$ can be determined from the following moment balance equation, wherein the moments are summed about point A in a clockwise direction:

$$(x_L \cdot F_L) + (x_R \cdot F_R) - (L \cdot R_C) = 0 \quad (6)$$

where:

$x_R$: distance measured from a reference point at the outer edge of the first force plate to the point of application of the force $F_R$ exerted on the second measurement surface by the right foot of the subject.

Then, in order to solve for the desired unknown quantity $x_R$, the terms of equation (6) are rearranged as follows:

$$x_R = \frac{(L \cdot R_C) - (x_L \cdot F_L)}{F_R} \quad (7)$$

Figure 18:
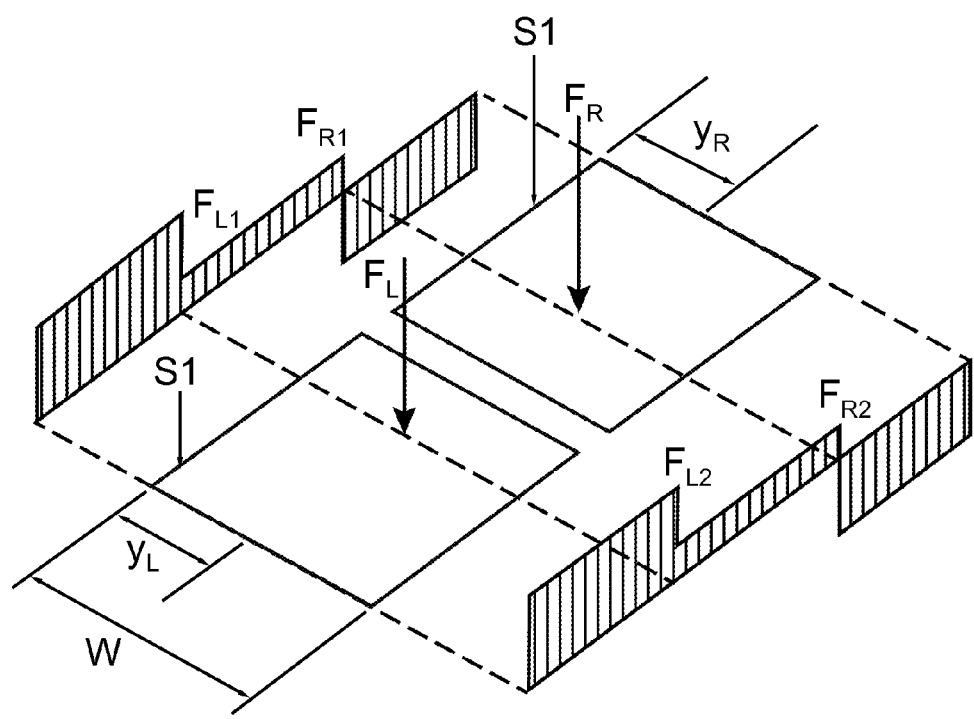
FIG. 18 is a three-dimensional (3-D) free body diagram/shear diagram that diagrammatically represents the forces acting on the dual force plate assembly according to an exemplary embodiment of the invention so as to illustrate the manner in which the y-coordinates of the center-of-pressure are determined.

Once the forces $F_L$ and $F_R$ and the x-coordinates of the center of pressure for each foot of the subject have been determined in the manner delineated above, a computational method that can be carried out by the data acquisition/data processing device 104 to compute the y-coordinates of the center of pressure for each foot of the subject will be explained with reference to the three-dimensional (3-D) free body diagram/shear diagram of FIG. 18. When broken down into their constituent components, the forces exerted on the first and second force plates by the respective left and right feet of the subject are described by the following two equations:

$$F_L = F_{L1} + F_{L2} \quad (8)$$

$$F_R = R_{R1} + R_{R2} \quad (9)$$

where:

$F_L$: force exerted on the surface of the first force plate by the left foot of the subject;

$F_{L1}$: first constituent component of the force exerted on the surface of the first force plate by the left foot of the subject;

$F_{L2}$: second constituent component of the force exerted on the surface of the first force plate by the left foot of the subject;

$F_R$: force exerted on the surface of the second force plate by the right foot of the subject;

$F_{R1}$: first constituent component of the force exerted on the surface of the second force plate by the right foot of the subject; and $F_{R2}$: second constituent component of the force exerted on the surface of the second force plate by the right foot of the subject.

Then, the unknown coordinate $y_L$ can be determined from the following moment balance equation, wherein the moments are summed about a point on a first side S1 of the first force plate in a clockwise direction:

$$(F_L \cdot y_L) - (F_{L2} \cdot W) = 0 \quad (10)$$

where:

$y_L$: distance measured from a reference point on the first side S1 of the first force plate to the point of application of the force $F_L$ exerted on the measurement surface by the left foot of the subject; and W: width of the dual force plate assembly.

Next, in order to solve for the desired unknown quantity $y_L$, the terms of equation (10) are rearranged as follows:

$$y_L = W \cdot \left(\frac{F_{L2}}{F_L}\right) \quad (11)$$

Following a similar procedure, the last unknown parameter $y_R$ can be determined from the following moment balance equation, wherein the moments are summed about a point on a first side S1 of the second force plate in a clockwise direction:

$$(F_R \cdot y_R) - (F_{R2} \cdot W) = 0 \qquad (12)$$

where:
$y_R$: distance measured from a reference point on the first side S1 of the second force plate to the point of application of the force $F_R$ exerted on the second measurement surface by the right foot of the subject.

Next, in order to solve for the desired unknown quantity $y_R$, the terms of equation (12) are rearranged as follows:

$$y_R = W \cdot \left(\frac{F_{R2}}{F_R}\right) \qquad (13)$$

Therefore, all of the unknown parameters of the dual force plate system are mathematically determined in the manner explained above by the data acquisition/data processing device 104. In a preferred embodiment of the invention, the data acquisition/data processing device 104 is specially programmed to perform all of these abovedescribed calculations.

G. Sixth Embodiment

Figure 19:
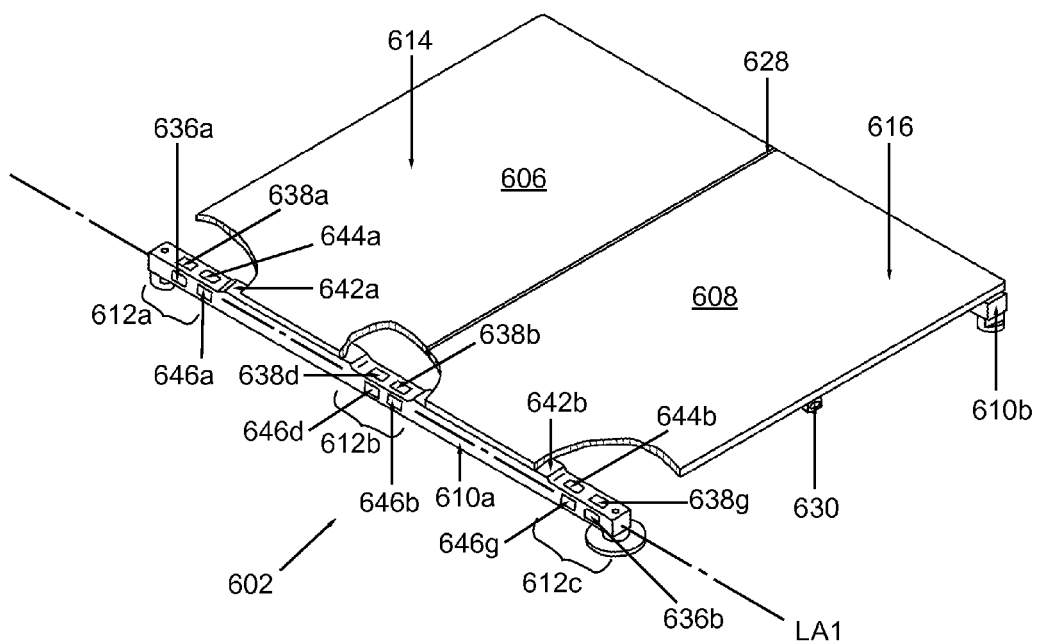
FIG. 19 is a cut-away perspective view of the dual force plate assembly of the dual force plate system according to a sixth embodiment of the invention.
Figure 20:
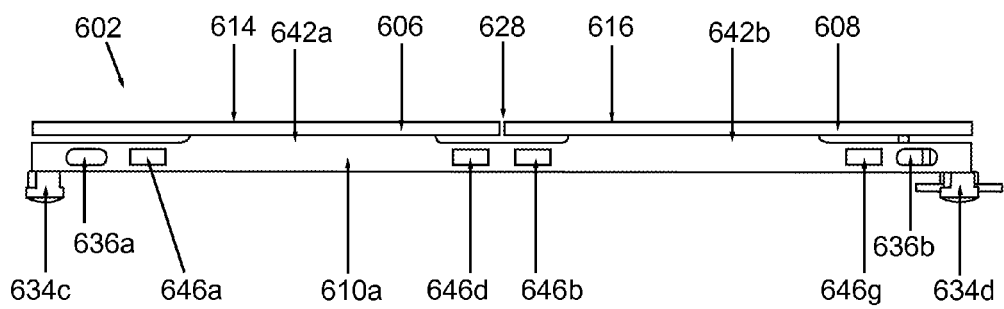
FIG. 20 is a side view of the dual force plate assembly of the dual force plate system according to the sixth embodiment of the invention.
Figure 21:
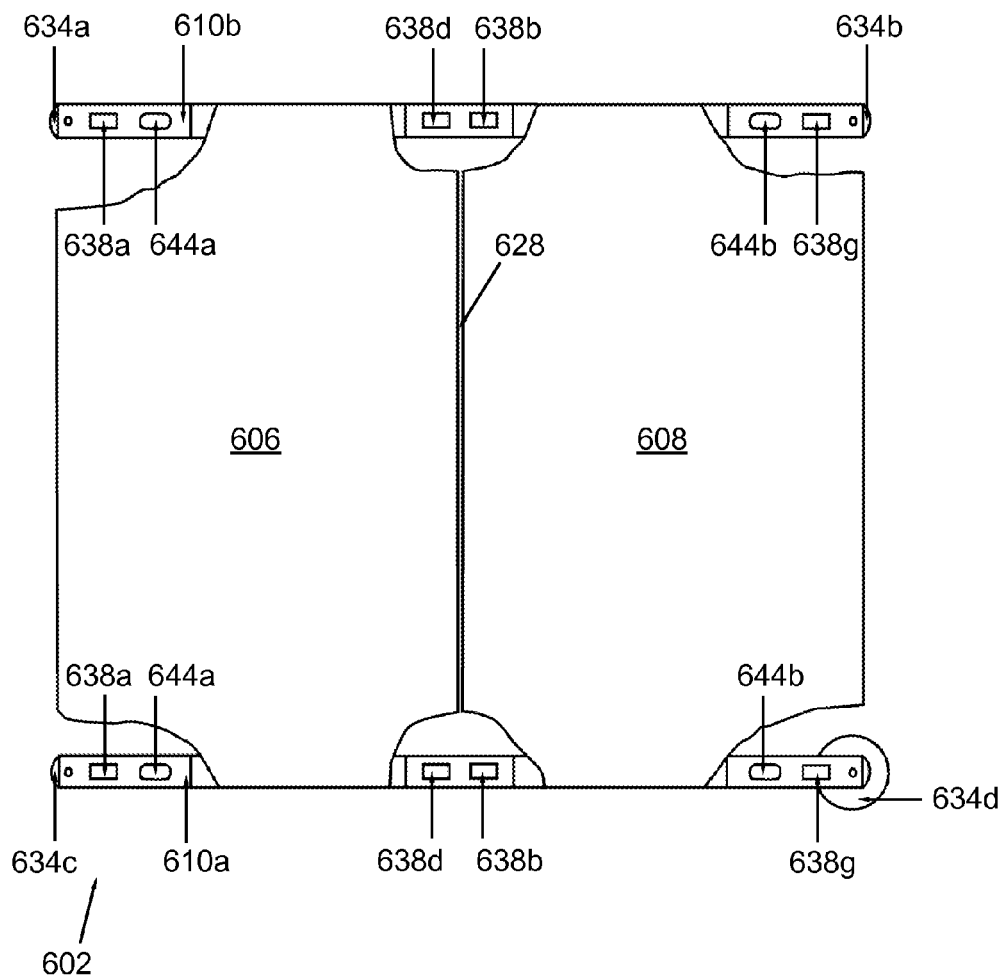
FIG. 21 is a cut-away top view of the dual force plate assembly of the dual force plate system according to the sixth embodiment of the invention.

A sixth embodiment of the dual force plate assembly is seen generally at 602 in FIGS. 19-21. In accordance with the sixth embodiment of the invention, the dual force plate assembly 602 for receiving a subject includes a first plate component 606, a second plate component 608, and continuous force transducer beams 610a, 610b mounted on opposite lateral sides of the first plate component 606 and second plate component 608. Unlike the force transducer beams described in conjunction with the aforedescribed embodiments of the invention, the force transducer beams 610a, 610b are capable of measuring the vertical force components and moments, as well as shear force components and moments. As explained above in conjunction with the preceding embodiments, the first plate component 606 has a top surface 614 that is configured to receive a first portion of a body of a subject. Similarly, the second plate component 608 has a top surface 616 that is configured to receive a second portion of a body of a subject. Also, similar to the embodiments described above, a narrow gap 628 is provided between the first plate component 606 and the second plate component 608 so as to prevent interaction between the two plate components 606, 608. Similar to the preceding embodiments, the dual force plate assembly 602 contains a port 630 for receiving the electrical cable 126.

Referring to FIGS. 19-21, it can be seen that each continuous force transducer beam 610a, 610b is attached to the underside of the first and second plate components 606, 608. In particular, as best shown in FIGS. 19 and 20, it can be seen that the top surface of each continuous force transducer beam 610a, 610b is provided with two protruding portions 642a, 642b. The protruding portions 642a, 642b are spaced apart from one another along the length of each continuous force transducer beam 610a, 610b. The top surface of the first protruding portion 642a on each of the continuous force transducer beams 610a, 610b is fixedly attached to the bottom surface of the first plate component 606, whereas the top surface of the second protruding portion 642b on each of the continuous force transducer beams 610a, 610b is fixedly attached to the bottom surface of the second plate component 608. It is highly advantageous that the first and second plate components 606, 608 only be connected to the protruding portions 642a, 642b of the continuous force transducer beams 610a, 610b so as to ensure that the total load applied to the top surfaces 614, 616 of the plate components 606, 608 is only transmitted through the force transducer components 612a, 612b, 612c. As explained above, each force transducer beam 610a, 610b can be fixedly attached to each plate component 606, 608 by utilizing a plurality of different attachment means such as, but not limited to, threaded fasteners (e.g., screws) or different types of suitable adhesives (e.g., an adhesive designed for bonding metallic components to one another).

As best illustrated in FIGS. 20 and 21, each force transducer beam 610a, 610b is provided with respective support feet 634c, 634d and 634a, 634b disposed at opposed longitudinal ends thereof. In the illustrated embodiment, the first of the two transducer beams 610a is provided with one non-adjustable support foot 634c near a first longitudinal end thereof and one adjustable support foot 634d near the other longitudinal end thereof, while the second of the two force transducer beams 610b is provided with two (2) non-adjustable support feet 634a, 634b disposed at opposed longitudinal ends thereof. The dual force plate assembly 602 is designed to be installed on a floor of a building or on any other rigid surface. The adjustable support foot 634d facilitates the leveling of the dual force plate assembly 602 on an uneven surface.

In the cut-away perspective view illustrated in FIG. 19, it can be seen that the first of the two transducer beams 610a is provided with three force transducer components 612a, 612b, 612c disposed along the length thereof. As shown in this figure, each of these three force transducer components 612a, 612b, 612c is linearly arranged along a longitudinal axis LA1, and each of these three force transducer components 612a, 612b, 612c intersects the longitudinal axis LA1. The first transducer component 612a is disposed at a first longitudinal end of the first transducer beam 610a. In the illustrated embodiment of the invention, the first transducer component 612a comprises a longitudinal segment of the force transducer beam 610a, a first aperture 636a disposed generally transversely through the longitudinal segment of the force transducer beam 610a, a second aperture 644a disposed generally vertically through the longitudinal segment of the force transducer beam 610a, a first plurality of strain gages 638a secured to the outer, top surface of the longitudinal segment of the force transducer beam 610a and substantially centered on the aperture 636a, and a second plurality of strain gages 646a secured to the outer, side surface of the longitudinal segment of the force transducer beam 610a and substantially centered on the aperture 644a. The first plurality of strain gages 638a together with the longitudinal segment of the force transducer beam 610a containing the first aperture 636a forms the vertical force transducer element of the first transducer component 612a, while the second plurality of strain gages 646a together with the longitudinal segment of the force transducer beam 610a containing the second aperture 644a forms the shear force transducer element of the first transducer component 612a.

The outer, top surface of the first transducer component 612a on which the first plurality of strain gages 638a is disposed is generally opposite to the inner top surface of the aperture 636a, while the outer, side surface of the first transducer component 612a on which the second plurality of strain gages 646a is disposed is generally opposite to the inner side surface of the aperture 644a. When a load is applied to the first plate component 606, the load is transferred to the longitudinal segment of the force transducer beam 610a that is associated with the first transducer component 612a; the longitudinal segment of the force transducer beam 610a operates as an elastically deformable structural member. The plurality of strain gages 638a is used to measure the deformation of the elastically deformable structural member (i.e., the longitudinal segment of the force transducer beam 610a) resulting from the vertical force applied to surface 614 of the plate component 606, while the plurality of strain gages 646a is used to measure the deformation of the elastically deformable structural member (i.e., the longitudinal segment of the force transducer beam 610a) resulting from the shear force applied to surface 614 of the plate component 606. While in the illustrated embodiment, the longitudinal segment of the force transducer beam 610a is provided with the first and second apertures 636a, 644a therein to maximize the beam deformation when the load is applied to the first plate component 606 by reducing the cross-sectional area of the beam 610a at the locations of the apertures 636a, 644a, it is to be understood that the invention is not so limited. Rather, in other embodiments of the invention, the longitudinal segment of the force transducer beam 610a, which forms a component of the first transducer component 612a, is not provided with apertures disposed therein.

As shown in FIG. 19, the second transducer component 612b is disposed in a central region of the force transducer beam 610a. The second transducer component 612b includes: (i) a longitudinal segment of the force transducer beam 610a; (ii) first and second pluralities of strain gages 638b, 638c secured to the respective outer top and bottom surfaces of the longitudinal segment of the force transducer beam 610a; (iii) third and fourth pluralities of strain gages 638d, 638f, which are longitudinally spaced apart from the first and second pluralities of strain gages 638b, 638c, secured to the respective outer top and bottom surfaces of the longitudinal segment of the force transducer beam 610a; (iv) fifth and sixth pluralities of strain gages 646b, 646c secured to the respective outer and inner side surfaces of the longitudinal segment of the force transducer beam 610a; (v) seventh and eighth pluralities of strain gages 646d, 646f, which are longitudinally spaced apart from the fifth and sixth pluralities of strain gages 646b, 646c, secured to the respective outer and inner side surfaces of the longitudinal segment of the force transducer beam 610a. The first and second pluralities of strain gages 638b, 638c measure the bending moment imparted on second transducer component 612b at a first location by a vertical force applied to first plate component 606 and second plate component 608 (see FIGS. 19 and 22). Similarly, the third and fourth pluralities of strain gages 638d, 638f measure the bending moment imparted on second transducer component 612b at a second location by a vertical force applied to first plate component 606 and second plate component 608 (see FIGS. 19 and 22). In contrast, fifth and sixth pluralities of strain gages 646b, 646c measure the bending moment imparted on second transducer component 612b at a first location by a shear force applied to first plate component 606 and second plate component 608 (see FIGS. 19 and 22), and seventh and eighth pluralities of strain gages 646d, 646f measure the bending moment imparted on second transducer component 612b at a second location by a shear force applied to first plate component 606 and second plate component 608 (see FIGS. 19 and 22). As such, the vertical force transducer element of the second transducer component 612b comprises the first, second, third, and fourth pluralities of strain gages 638b, 638c, 638d, 638f, while the shear force transducer element of the second transducer component 612b comprises the fifth, sixth, seventh, and eighth pluralities of strain gages 646b, 646c, 646d, 646f.

Figure 22:
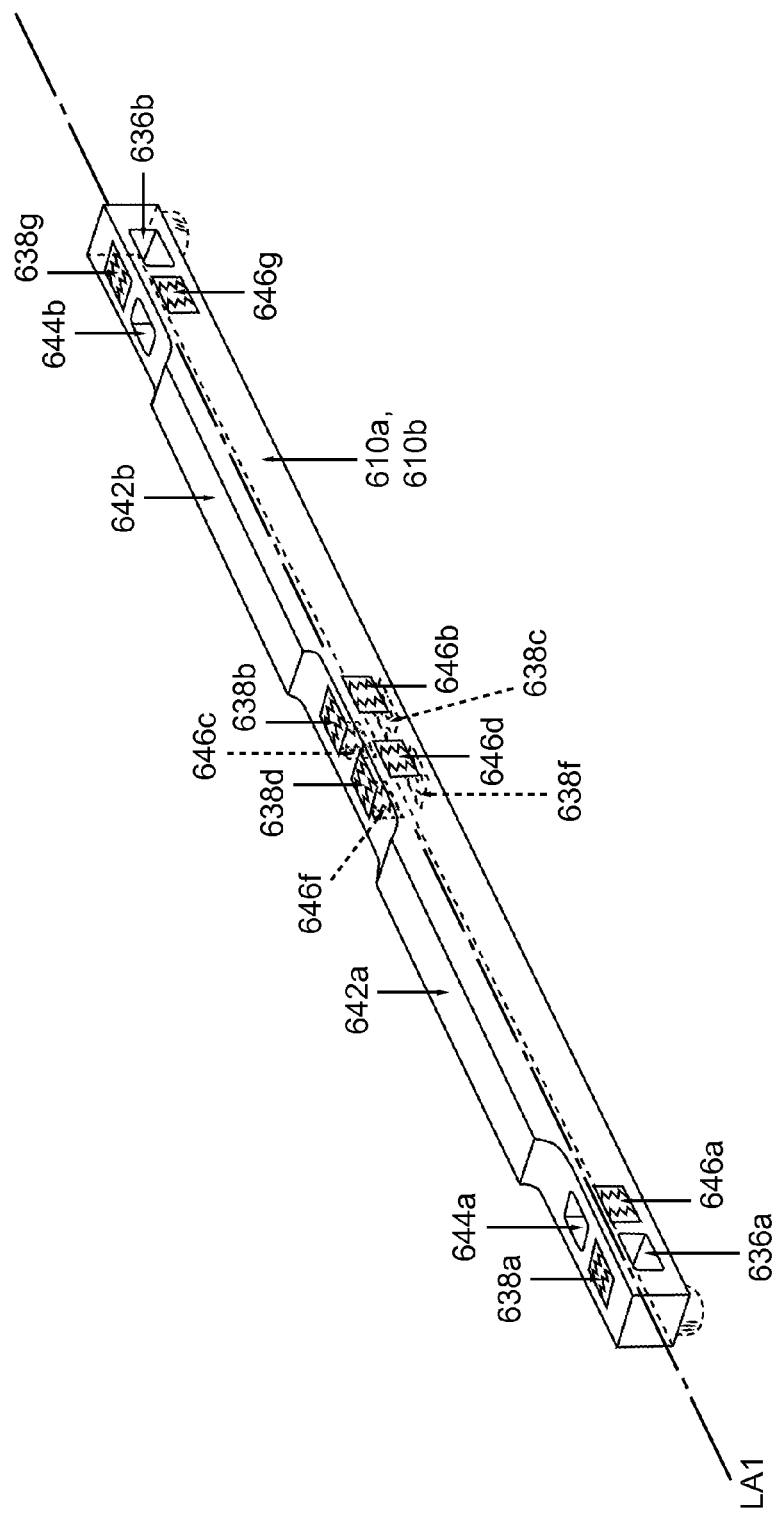
FIG. 22 is a perspective view of a transducer beam of the dual force plate assembly according to the sixth embodiment of the invention.

As best illustrated in FIG. 22, the first and third pluralities of strain gages 638b, 638d, which are mounted on the outer, top surface of the second transducer component 612b, are substantially vertically aligned with respective second and fourth pluralities of strain gages 638c, 638f, which are mounted on the outer, bottom surface of the second transducer component 612b. Similarly, the fifth and seventh pluralities of strain gages 646b, 646d, which are mounted on the outer, side surface of the second transducer component 612b, are substantially horizontally aligned with respective sixth and eighth pluralities of strain gages 646c, 646f, which are mounted on the inner, side surface of the second transducer component 612b. When the second transducer component 612b undergoes bending due to the application of a vertical force on plate components 606, 608, the first and third pluralities of strain gages 638b, 638d are configured to measure the deformation of the segmental portion of the force transducer beam 610a due to compression, while the second and fourth pluralities of strain gages 638c, 638f are configured to measure the deformation of the segmental portion of the force transducer beam 610a due to tension. Similarly, depending on the direction in which the shear force is being applied to the plate components 606, 608, one pair of the strain gages 646b, 646c, 646d, 646f is configured to measure the deformation of the segmental portion of the force transducer beam 610a due to compression, and the other pair of the strain gages 646b, 646c, 646d, 646f is configured to measure the deformation of the segmental portion of the force transducer beam 610a due to tension.

Referring again to FIG. 19, it can be seen that a third transducer component 612c is disposed at a second longitudinal end of the first transducer beam 610a, which is opposite to its first longitudinal end on which the first transducer component 612a is disposed. In other words, the third transducer component 612c is generally in a mirrored relationship with respect to the first transducer component 612a. Like the first transducer component 612a, the third transducer component 612c comprises a longitudinal segment of the force transducer beam 610a, a first aperture 636b disposed generally transversely through the longitudinal segment of the force transducer beam 610a, a second aperture 644b disposed generally vertically through the longitudinal segment of the force transducer beam 610a, a first plurality of strain gages 638g secured to the outer, top surface of the longitudinal segment of the force transducer beam 610a and substantially centered on the aperture 636b, and a second plurality of strain gages 646g secured to the outer, side surface of the longitudinal segment of the force transducer beam 610a and substantially centered on the aperture 644b. Also, similar to that described above for the first transducer component 612a, the first plurality of strain gages 638g together with the longitudinal segment of the force transducer beam 610a containing the first aperture 636b forms the vertical force transducer element of the third transducer component 612c, while the second plurality of strain gages 646g together with the longitudinal segment of the force transducer beam 610a containing the second aperture 644b forms the shear force transducer element of the third transducer component 612c. The third transducer component 612c functions in the same manner as described above for the first transducer component 612a, except that the third transducer component 612c measures the vertical and shear forces resulting from a load being applied to the second plate component 608, rather than the first plate component 606.

As shown in FIGS. 19 and 21, a second force transducer beam 610b is mounted on a side of the bottom surface of the first and second plate components 606, 608 that is opposite to the side of the bottom surface on which the first force transducer beam 610a is mounted. The second force transducer beam 610b is generally a mirror image of the first force transducer beam 610a Like the first force transducer beam 610a, the second force transducer beam 610b contains first, second, and third force transducer components 612a, 612b, 612c disposed along the length thereof with the same apertures 636a, 636b, 644a, 644b and pluralities of strain gages 638a-638d, 638f-638g, 646a-646d, 646f-646g described in conjunction with the first force transducer beam 610a.

H. Seventh Embodiment

Figure 23:
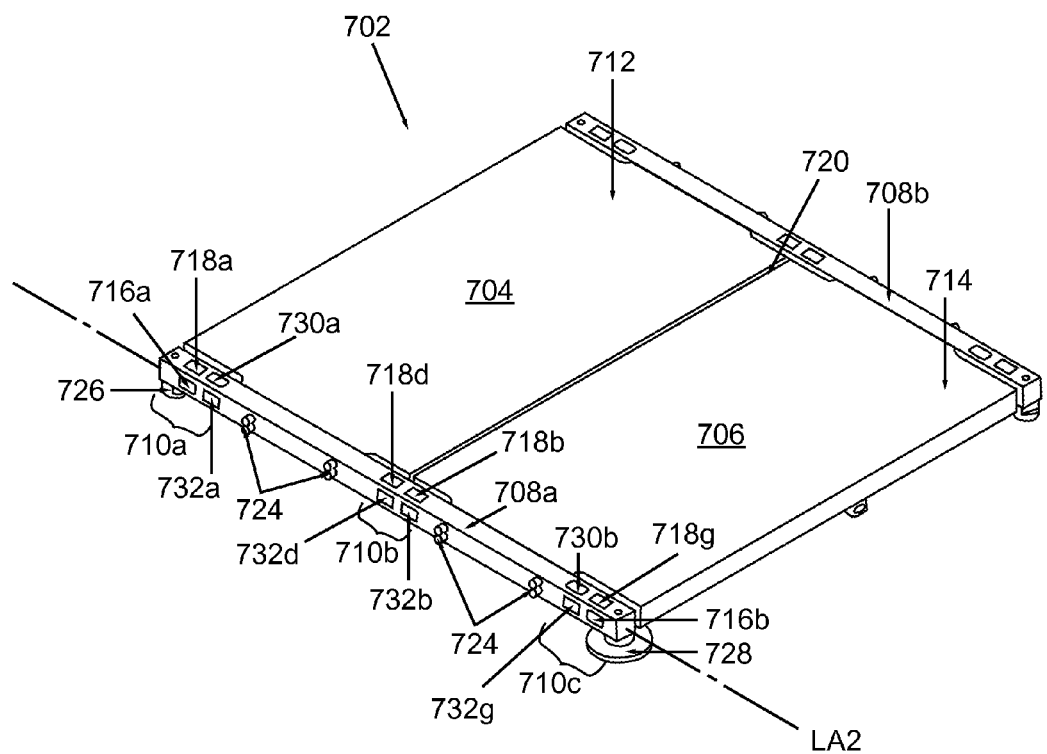
FIG. 23 is a perspective view of a dual force plate assembly of the dual force plate system according to a seventh embodiment of the invention.
Figure 24:
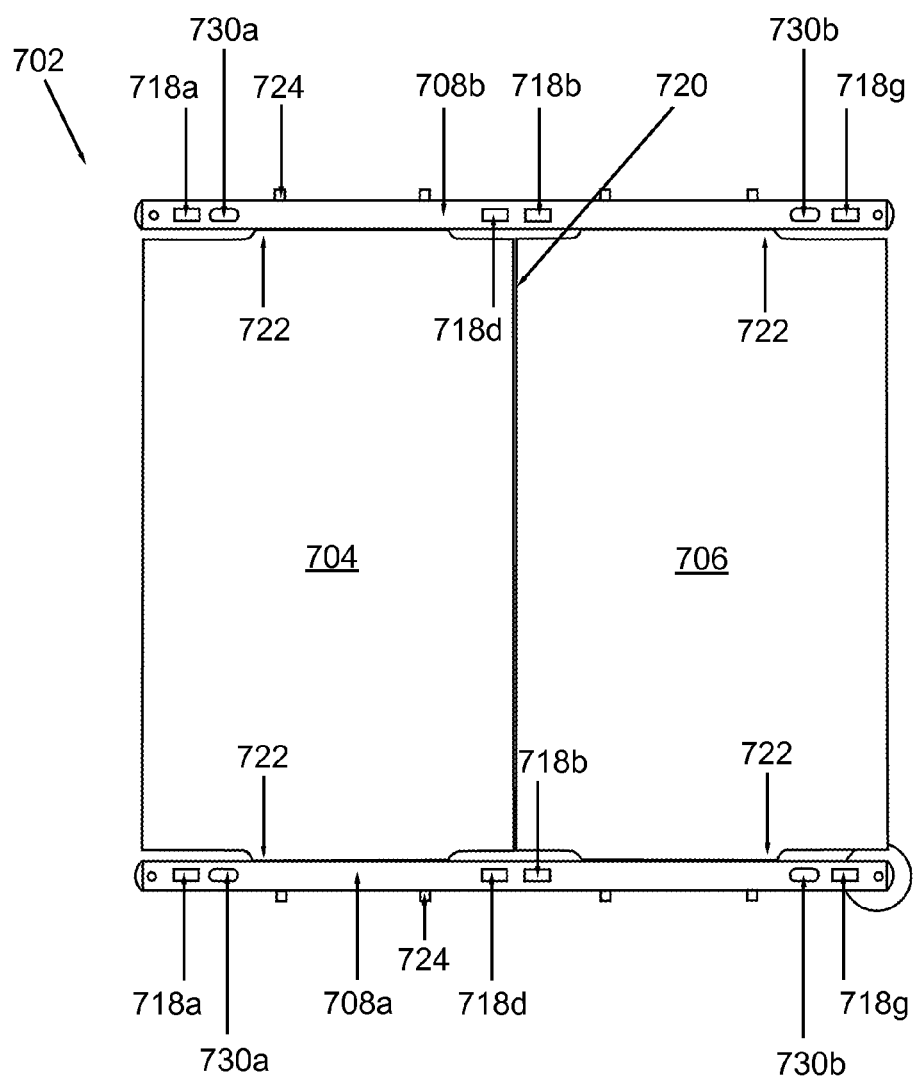
FIG. 24 is a top view of the dual force plate assembly of the dual force plate system according to the seventh embodiment of the invention.

A seventh embodiment of the dual force plate assembly is seen generally at 702 in FIGS. 23 and 24. In accordance with the seventh embodiment of the invention, the dual force plate assembly 702 for receiving a subject utilizes continuous force transducer beams 708a, 708b disposed on opposite lateral sides of the first and second plate components 704, 706, rather than force transducer beams disposed underneath the first and second plate components as described with regard to the sixth embodiment of the invention. As explained above in conjunction with the preceding embodiments, the first plate component 704 has a top surface 712 that is configured to receive a first portion of a body of a subject. Similarly, the second plate component 706 has a top surface 714 that is configured to receive a second portion of a body of a subject. Also, similar to the embodiments described above, a narrow gap 720 is provided between the first plate component 704 and the second plate component 706 so as to prevent interaction between the two plate components 704, 706.

Advantageously, in a preferred embodiment, the dual force plate assembly 702 has an overall height that is significantly lower than conventional force plates used in balance assessment. This reduction in height is made possible, in part, by the mounting of the continuous force transducer beams 708a, 708b on the lateral sides of the first and second plate components 704, 706.

Referring to FIG. 23, it can be seen that each continuous force transducer beam 708a, 708b includes a plurality of force transducer components 710a, 710b, 710c disposed along the length thereof. As shown in this figure, each of these three force transducer components 710a, 710b, 710c is linearly arranged along a longitudinal axis LA2, and each of these three force transducer components 710a, 710b, 710c intersects the longitudinal axis LA2. Also, similar to the sixth embodiment of the invention, the first and third force transducer components 710a, 710c are provided with apertures 716a, 716b, 730a, 730b disposed therethrough. Moreover, as in the sixth embodiment, the outer transducer components 710a, 710c measure the vertical and shear forces exerted on the first and second plate components 704, 706, respectively, whereas the centrally disposed transducer components 710b measure the bending moments due to vertical and shear forces resulting from a load being applied to the first and second plate components 704, 706. In FIG. 23, it can be seen that the centrally disposed transducer components 710b extend across the gap 720 between the first plate component 704 and the second plate component 706 (i.e., the centrally disposed transducer components 710b bridge the gap 720 between the first plate component 704 and the second plate component 706).

Figure 25:
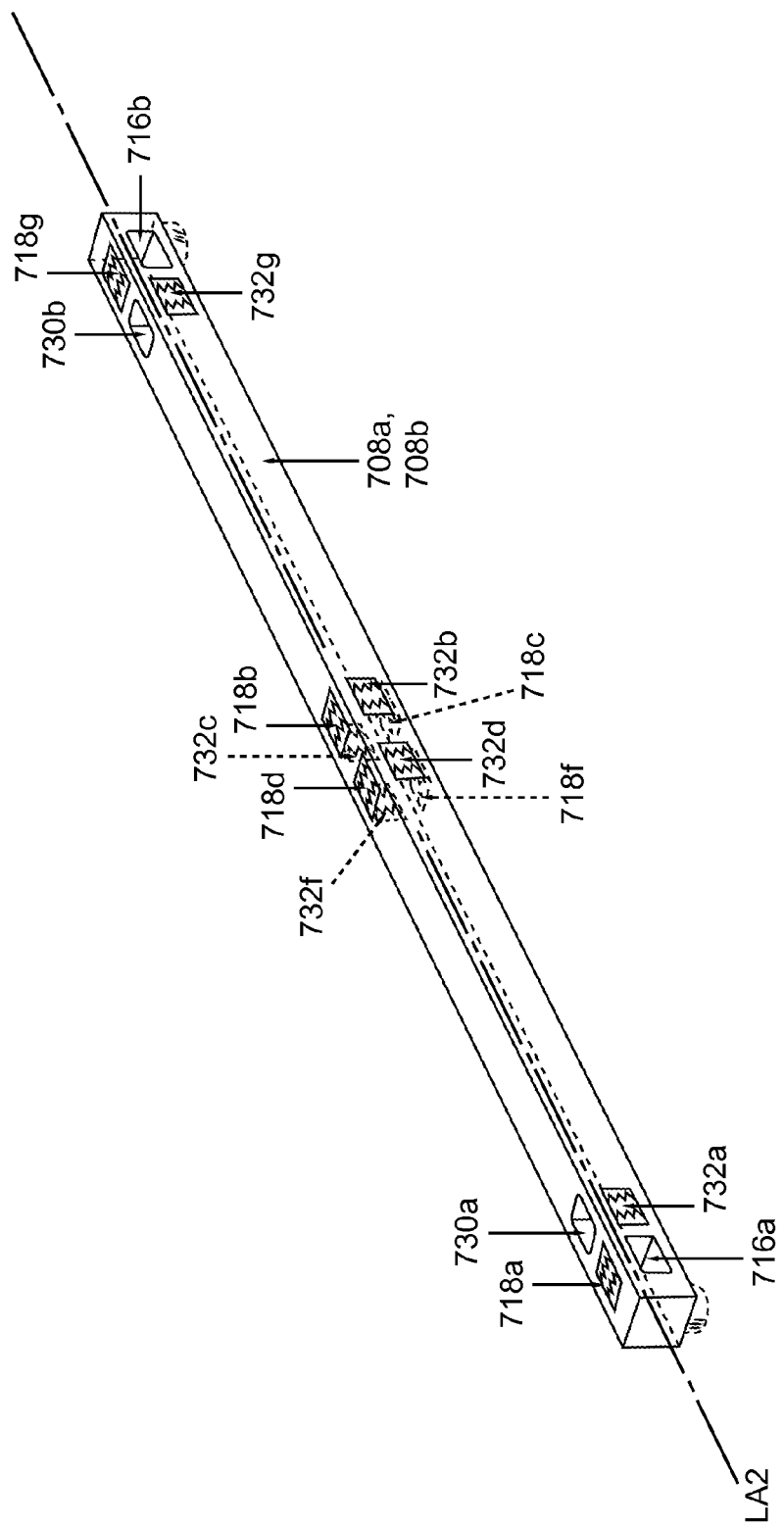
FIG. 25 is a perspective view of a transducer beam of the dual force plate assembly according to the seventh embodiment of the invention.

Like the force transducer elements 612a described above with regard to the sixth embodiment of the invention, each first force transducer element 710a is provided with a plurality of strain gages 718a secured to the outer, top surface of its associated force transducer beam 708a, 708b, and substantially centered on the aperture 716a (see FIGS. 23 and 24), and a plurality of strain gages 732a secured to the outer, side surface of its associated force transducer beam 708a, 708b and substantially centered on the aperture 730a. Also, similar to the force transducer elements 612c of the sixth embodiment, each force transducer element 710c is provided with a plurality of strain gages 718g secured to the outer, top surface of its associated force transducer beam 708a, 708b and substantially centered on the aperture 716b (see FIGS. 23 and 24), and a plurality of strain gages 732g secured to the outer, side surface of its associated force transducer beam 708a, 708b and substantially centered on the aperture 730b. In addition, like the force transducer elements 612b of the sixth embodiment of the invention, each force transducer element 710b is provided with first and second pluralities of strain gages 718b, 718c secured to the respective outer top and bottom surfaces of its associated force transducer beam 708a, 708b; third and fourth pluralities of strain gages 718d, 718f, which are longitudinally spaced apart from the first and second pluralities of strain gages 718b, 718c, secured to the respective outer top and bottom surfaces of its associated force transducer beam 708a, 708b; fifth and sixth pluralities of strain gages 732b, 732c secured to the respective outer and inner side surfaces of its associated force transducer beam 708a, 708b; seventh and eighth pluralities of strain gages 732d, 732f, which are longitudinally spaced apart from the fifth and sixth pluralities of strain gages 732b, 732c, secured to the respective outer and inner side surfaces of the longitudinal segment of its associated force transducer beam 708a, 708b (see FIGS. 23 and 25). As described above, the first, second, third, and fourth pluralities of strain gages 718b, 718c, 718d, 718f measure the bending moment due to the vertical force, while the fifth, sixth, seventh, and eighth pluralities of strain gages 732b, 732c, 732d, 732f measure the bending moment due to the shear force (refer to FIGS. 23 and 25).

Referring to FIGS. 23 and 24, it can be seen that each continuous force transducer beam 708a, 708b is fixedly attached to adjacent lateral sides of the first and second plate components 704, 706 using a plurality of screws 724. In particular, as best shown in the top view of FIG. 24, each force transducer beam 708a, 708b is attached to a respective centrally disposed protruding portion 722 on opposite lateral sides of the first plate component 704 and the second plate component 706. It is highly advantageous that the force transducer beams 708a, 708b only be connected to the centrally disposed protruding portions 722 of the first and second plate component 704, 706 so as to ensure that the total load applied to the top surfaces 712, 714 of the plate components 704, 706 is only transmitted through the force transducer elements 710a, 710b, 710c on each side thereof. In FIG. 23, a total of four (4) screws 724 are used to connect each force transducer beam 708a, 708b to each plate component 704, 706. However, it is to be understood that the invention is not so limited. Rather, in other embodiments of the invention, more than four screws or less than four screws could be used to fixedly attach each force transducer beam 708a, 708b to each force plate component 704, 706. In yet other embodiments of the invention, the force transducer beams 708a, 708b could be connected to plate components 704, 706 by using different types of suitable adhesives (e.g., an adhesive designed for bonding metallic components to one another).

As best depicted in FIG. 23, the top surface 712 of the first plate component 704 and the top surface 714 of the second plate component 706 are both substantially aligned with the top surfaces of the transducer beams 708a, 708b in a preferred embodiment of the invention. This design feature enables the profile of the dual force plate assembly 702 to be minimized so that subjects are able to easily step on and off the dual force plate assembly 702. Also, it prevents the transducer beams 708a, 708b from posing a tripping hazard to subjects, as would be the case if the top surfaces of the transducer beams 708a, 708b were disposed above the top surfaces 712, 714 of the first and second plate components 704, 706. However, it is to be understood that the invention is not so limited. For example, in other embodiments of the invention, the top surfaces of the transducer beams 708a, 708b could be disposed below the top surfaces 712, 714 of the first and second plate components 704, 706.

In the seventh embodiment of the invention, each force transducer beam 708a, 708b is provided with respective support feet disposed at opposed longitudinal ends thereof. In FIG. 23, it can be seen that the first of the two transducer beams 708a is provided with one non-adjustable support foot 726 near a first longitudinal end thereof and one adjustable support foot 728 near the other longitudinal end thereof. The bottom portion of the second of the two force transducer beams 708b is not explicitly shown in FIG. 23, but it is provided with two (2) non-adjustable support feet disposed at opposed longitudinal ends thereof, both of which are generally the same as non-adjustable support foot 726. The dual force plate assembly 702 is designed to be installed on a floor of a building or on any other rigid surface. The adjustable support foot 728 facilitates the leveling of the dual force plate assembly 702 on an uneven surface.

I. Additional Computations Performed by the Data Acquisition/Data Processing Device 104

Next, the manner in which the data acquisition/data processing device 104 calculates the applied shear forces and the center of gravity for the subject will be explained in detail. Initially, referring to FIGS. 26, 27A-27B, and 28A-28C, the mathematical determination of the horizontally-oriented shear forces for each foot of the subject will be explained. Then, with reference to FIGS. 29-31, the determination of the center-of-gravity for the subject will be described.

FIG. 26 depicts a diagrammatic bottom view of a dual force plate assembly of a dual force plate system, wherein the measured parameters are depicted thereon. The cross-hatched regions 10 diagrammatically denote the attachment locations of the transducer beams to the plate components. With reference to FIG. 26, the equations describing the shear-related measurements made by the force transducer beams of the dual force plate are written as follows:

$$S_L = S_{L1} + S_{L2} \tag{14}$$

$$S_R = S_{R1} + S_{R2} \tag{15}$$

$$M_L = M_{L1} + M_{L2} \tag{16}$$

$$M_R = M_{R1} + M_{R2} \tag{17}$$

where:
$S_L$: total shear force measured by the first (left) force transducer elements disposed on opposite sides of the dual force plate;
$S_R$: total shear force measured by the second (right) force transducer elements disposed on opposite sides of the dual force plate;
$S_{L1}$: shear force measured by the first (left) force transducer element on the first side of the dual force plate;
$S_{L2}$: shear force measured by the first (left) force transducer element on the second side of the dual force plate;
$S_{R1}$: shear force measured by the second (right) force transducer element on the first side of the dual force plate;
$S_{R2}$: shear force measured by the second (right) force transducer element on the second side of the dual force plate;
$M_L$: left bending moment due to the shear force measured by the third force transducer elements (i.e. between the two plates) disposed on opposite sides of the dual force plate;
$M_R$: right bending moment due to the shear force measured by the third force transducer elements (i.e. between the two plates) disposed on opposite sides of the dual force plate;
$M_{L1}$: left plate bending moment due to the shear force measured by the third force transducer element (i.e. between the two plates) on the first side of the dual force plate;
$M_{L2}$: left plate bending moment due to the shear force measured by the third force transducer element (i.e. between the two plates) on the second side of the dual force plate;
$M_{R1}$: right plate bending moment due to the shear force measured by the third force transducer element (i.e. between the two plates) on the first side of the dual force plate; and
$M_{R2}$: right plate bending moment due to the shear force measured by the third force transducer element (i.e. between the two plates) on the second side of the dual force plate.

Figures 28A, 28B, 28C:
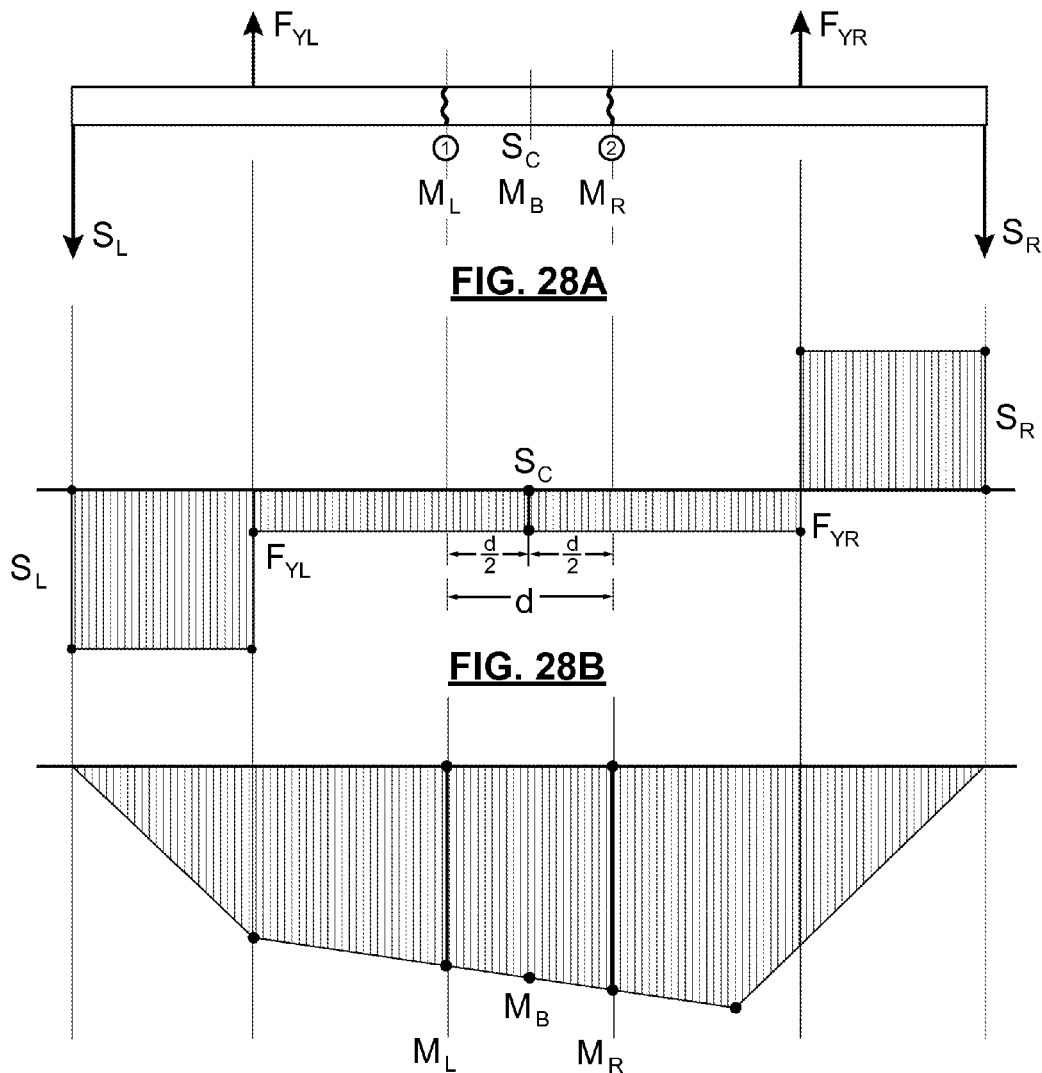
FIG. 28A is a free body diagram of a beam that diagrammatically represents the shear forces and moments acting on the dual force plate assembly according to another exemplary embodiment of the invention.
FIG. 28B is a shear diagram that diagrammatically represents the shear forces acting on the dual force plate assembly according to another exemplary embodiment of the invention.
FIG. 28C is a moment diagram that diagrammatically represents the moments acting on the dual force plate assembly according to another exemplary embodiment of the invention.
Figure 29:
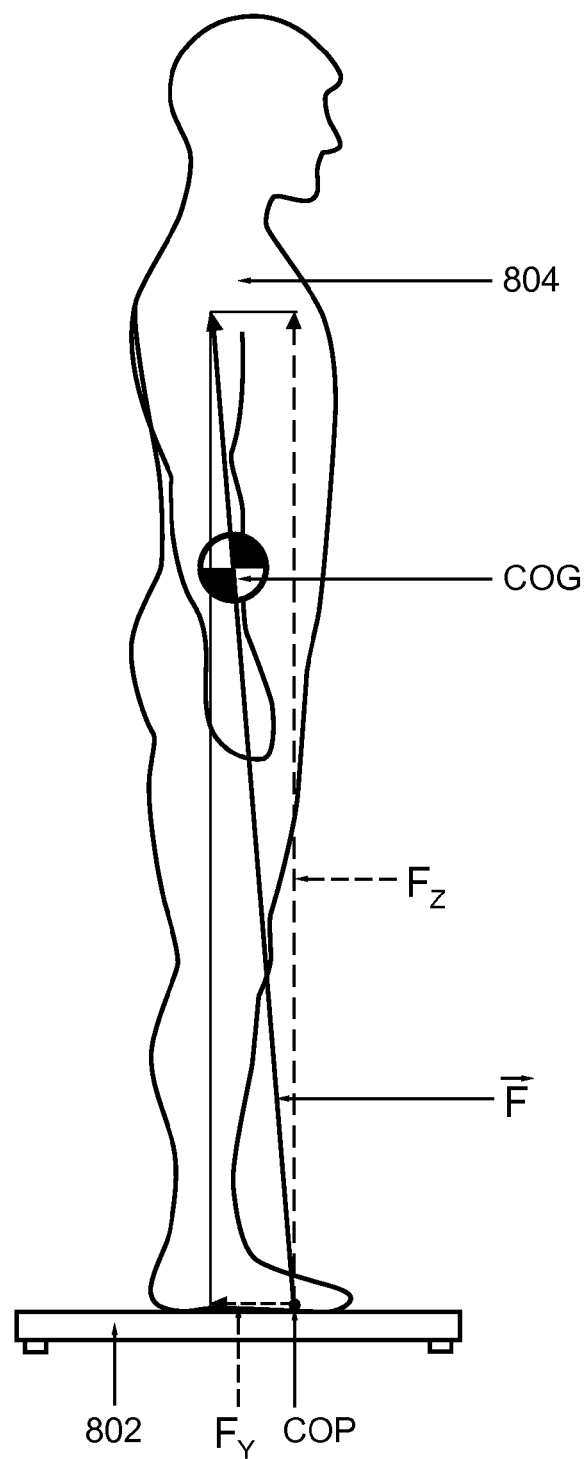
FIG. 29 is a diagrammatic side view of a subject disposed on a surface of a force plate, wherein the center of pressure (COP) and the center of gravity (COG) of the subject are depicted thereon along with the vertical force and shear force components.

In FIG. 28A, a free diagram body of the dual force plate assembly is shown in order to graphically illustrate measured shear-related parameters of the system and unknown shear forces $F_{YL}$, $F_{YR}$ being applied to the force plate by the subject. Referring to this figure, it can be seen that the dual force plate assembly is being modeled as one continuous, simply supported beam. The dual force plate assembly can be accurately modeled as a single beam because the transducer beams, each of which operatively connects the first plate to the second plate, are fixedly attached to the bottom surfaces of the first and second plates. Thus, even though separate components are utilized in the actual assembly, the dual force plate operates as if it is a single structure. As depicted in FIGS. 28A and 28B, the shear force $S_L$ acting on the left end of the assembly is sensed by first force transducer elements, while the shear force $S_R$ acting on the right end of the assembly is measured by second force transducer elements. The third force transducer elements, which are disposed proximate to the center of the transducer beam, can measure either the shear force $S_C$ and the moment $M_B$ or a left and right bending moment $M_L$, $M_R$ (i.e., they measure the load transferred between the first and second plates).

Now that both the unknown shear forces and the measured parameters of the dual force plate system have been defined, the mathematical equations for determining the unknown shear forces of the system can be formulated. As shown in FIGS. 27A and 27B, the dual force plate assembly represented diagrammatically by the beam in FIG. 28A, can be split into two separate beam sections for analysis purposes. The left beam section is illustrated in FIG. 27A, while the right beam section is depicted in FIG. 27B. Using the free body diagrams for the beam sections depicted in FIGS. 27A and 27B, the shear forces exerted on the first and second force plates by the respective left and right feet of the subject are described by the following two equations:

$$F_{YL} = S_L + S_C \tag{18}$$

$$F_{YR} = S_R - S_C \tag{19}$$

where:

$F_{YL}$: shear force exerted on the surface of the first plate component by the left foot of the subject;

$F_{YR}$: shear force exerted on the surface of the second plate component by the right foot of the subject;

$S_L$: total shear force measured by the first (left) force transducer elements disposed on opposite sides of the dual force plate;

$S_R$: total shear force measured by the second (right) force transducer elements disposed on opposite sides of the dual force plate; and $S_C$: total shear force measured by the third (center) force transducer elements disposed on opposite sides of the dual force plate.

Thus, the applied shear forces can be obtained by plugging the shear forces $S_L$, $S_R$, and $S_C$, which are measured by the force transducer elements, into equations (18) and (19) and then, solving for forces $F_{YL}$, and $F_{YR}$.

Alternatively, if each centrally disposed transducer element measures a right and left bending moment $M_R$, $M_L$, rather than the shear force and a single bending moment, then the shear force $S_C$ can be determined by utilizing the following equation:

$$S_C = \frac{(M_R - M_L)}{d} \quad (20)$$

where:

$M_L$: left bending moment due to the shear force measured by the third force transducer elements (i.e. between the two plates) disposed on opposite sides of the dual force plate (e.g., measured at a first location 1 on the beam—see FIG. 28A);

$M_R$: right bending moment due to the shear force measured by the third force transducer elements (i.e. between the two plates) disposed on opposite sides of the dual force plate (e.g., measured at a second location 2 on the beam—see FIG. 28A); and d: distance between the locations at which the respective right and left bending moments are measured (i.e., distance between first and second locations on the beam—see FIGS. 28A and 28B).

Then, the applied shear forces $F_{YL}$, $F_{YR}$ can be determined from equations (18) and (19) by using the computed shear force $S_C$ from equation (20) together with the measured shear forces $S_L$ and $S_R$.

Now, the manner in which the data acquisition/data processing device 104 calculates the center of gravity for the subject will be explained in detail. Initially, referring to FIG. 29, a side view of a subject 804 disposed on a surface of a force plate 802 is diagrammatically illustrated. As shown in this figure, the ground reaction force vector $\vec{F}$ passes through the center of pressure (COP) for the subject and the subject's center of gravity (COG). For the purpose of the analysis, the ground reaction force vector $\vec{F}$ can be represented by its constituent components, namely its vertical force component $F_Z$ and its shear force component $F_Y$. It is to be noted that, for the purposes of this analysis, only the sagittal plane of the subject is being considered.

Figure 30:
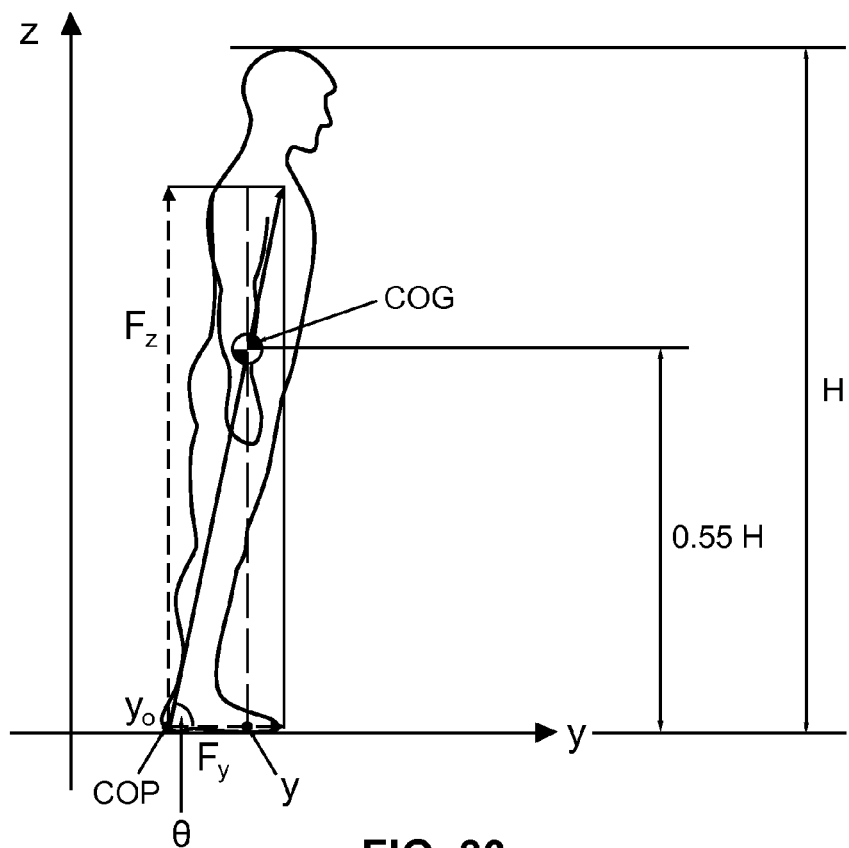
FIG. 30 is a free body diagram of a subject illustrating the force components and parameters that are used in computing center of gravity (COG) of the subject.

Then, with reference to FIG. 30, it can be seen that the y-coordinate (y) of the subject's center-of-gravity is the unknown parameter being computed by the data acquisition/data processing device 104. The center of pressure (COP) y-coordinate ($y_0$) is known from the force plate output (e.g., refer to the calculations described above in section F of the description). Also, as shown in FIG. 30, the following trigonometric relationship exists between the angle θ, the vertical force component $F_Z$, and the shear force component $F_Y$:

$$\tan\theta = \frac{F_Z}{F_Y} \quad (21)$$

Figure 31:
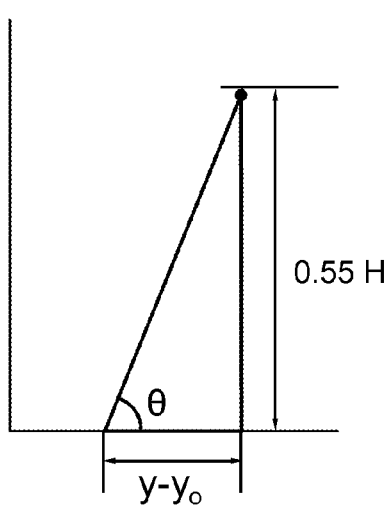
FIG. 31 is a trigonometric diagram that is used in computing center of gravity (COG) of the subject.

Now, turning to FIG. 31, it can be seen that the tangent of the angle θ is also equal to the following:

$$\tan\theta = \frac{0.55H}{y - y_0} \quad (22)$$

where:

H: height of the subject;

y: y-coordinate of the center of gravity (COG) of the subject; and $y_0$: y-coordinate of the center of pressure (COP) of the subject determined from the force plate output.

Thus, it follows that equations (21) and (22) can be combined to obtain the following relationship:

$$\frac{0.55H}{y - y_0} = \frac{F_Z}{F_Y} \quad (23)$$

This equation (23) can be initially rearranged as follows:

$$y - y_0 = \frac{F_Y}{F_Z}(0.55H) \quad (24)$$

Finally, to solve for the unknown y-coordinate (y) of the subject's center of gravity, equation (24) is rearranged in the following manner:

$$y - y_0 + \frac{F_Y}{F_Z}(0.55H) \quad (25)$$

Therefore, the y-coordinate (y) of the subject's center of gravity can then be determined as a function of the y-coordinate ($y_0$) of the subject's center of pressure, the shear force component $F_Y$, the vertical force component $F_Z$, and the height of the subject H. The y-coordinate ($y_0$) of the subject's center of pressure, the shear force component $F_Y$, and the vertical force component $F_Z$ are all determined from the output of the force plate, whereas the height of the subject can be entered into the data acquisition/data processing device 104 by the user of the system (i.e., after the system user acquires the height value from the subject being tested). Advantageously, the computational method described above enables the subject's center of gravity to be accurately determined using the force measurement system.

While the exemplary force plate systems explained above employ forces plate assemblies 102, 202, 302, 402, 502, 602, 702 that are configured to receive a subject in an upright position, it is to be understood that the invention is not so limited. Rather, the present invention can be practiced with a force plate assembly that measures the forces exerted by the limbs of a subject that is disposed in a position other than an upright position, such as subject in a substantially horizontal position. For example, a dual force assembly could be mounted on a vertical surface (e.g., the vertical side of a swimming pool) to measure the substantially horizontal forces exerted on the vertical surface by the arms and/or the legs of the subject.

Although the invention has been shown and described with respect to a certain embodiment or embodiments, it is apparent that this invention can be embodied in many different forms and that many other modifications and variations are possible without departing from the spirit and scope of this invention. For example, in some embodiments of the invention, a virtual reality system is provided in conjunction with the dual force plate system so that the subject can be tested while experiencing a variety of different simulated scenarios.

While exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A dual force plate system having two independent measurement surfaces, the dual force plate system comprising:
    a first plate component having a first measurement surface for receiving a first portion of a body of a subject, a first opposed surface that is disposed generally opposite to the first measurement surface, and a plurality of lateral surfaces that extend between the first measurement surface and the first opposed surface;
    a second plate component having a second measurement surface for receiving a second portion of the body of the subject, a second opposed surface that is disposed generally opposite to the second measurement surface, and a plurality of lateral surfaces that extend between the second measurement surface and the second opposed surface;
    a first force transducer element operatively coupled to either the first opposed surface of the first plate component or to one of the lateral surfaces of the first plate component, the first force transducer element configured to output at least one first quantity that is representative of a shear force being applied to the first measurement surface;
    a second force transducer element operatively coupled to either the second opposed surface of the second plate component or to one of the lateral surfaces of the second plate component, the second force transducer element configured to output at least one second quantity that is representative of a shear force being applied to the second measurement surface; and
    a third force transducer element operatively coupled to either the first opposed surface of the first plate component and the second opposed surface of the second plate component, or to one of the lateral surfaces of the first plate component and one of lateral surfaces of second plate component, the third force transducer element configured to output at least one third quantity that is representative of a load being transferred between the first plate component and the second plate component.

2. The dual force plate system according to claim 1, wherein either the first and third force transducer elements are both operatively coupled to the first opposed surface of the first plate component, or the first and third force transducer elements are both operatively coupled to the same lateral surface of the first plate component.

3. The dual force plate system according to claim 2, wherein either the second and third force transducer elements are both operatively coupled to the second opposed surface of the second plate component, or the second and third force transducer elements are both operatively coupled to the same lateral surface of the second plate component.

4. The dual force plate system according to claim 3 further comprising:
    a fourth force transducer element laterally spaced apart from the first force transducer element, the fourth force transducer element operatively coupled to either the first opposed surface of the first plate component or to another one of the lateral surfaces of the first plate component, the fourth force transducer element configured to output at least one fourth quantity that is representative of a shear force being applied to the first measurement surface;
    a fifth force transducer element laterally spaced apart from the second force transducer element, the fifth force transducer element operatively coupled to either the second opposed surface of the second plate component or to another one of the lateral surfaces of the second plate component, the fifth force transducer element configured to output at least one fifth quantity that is representative of a shear force being applied to the second measurement surface; and
    a sixth force transducer element laterally spaced apart from the third force transducer element, the sixth force transducer element operatively coupled to either the first opposed surface of the first plate component and the second opposed surface of the second plate component, or to another one of the lateral surfaces of the first plate component and another one of lateral surfaces of second plate component, the sixth force transducer element configured to output at least one sixth quantity that is representative of a load being transferred between the first plate component and the second plate component.

5. The dual force plate system according to claim 4, wherein the first, second, and third force transducer elements are generally symmetrically arranged with respect to the fourth, fifth, and sixth force transducer elements.

6. The dual force plate system according to claim 1, wherein the first force transducer element, the second force transducer element, and the third force transducer element are each part of a continuous beam force transducer assembly, the first, second and third force transducer elements being spaced apart along the length of the continuous beam force transducer assembly; and wherein the continuous beam force transducer assembly extends substantially the combined length of the first and second opposed surfaces of the first and second plate components, or the combined length of the lateral surfaces of the first and second plate components to which the first and second force transducer elements are respectively coupled.

7. The dual force plate system according to claim 1, wherein the first force transducer element is mounted in a cantilevered manner from the first plate component and the second force transducer element is mounted in a cantilevered manner from the second plate component.

8. The dual force plate system according to claim 1, further comprising a data processing device operatively coupled to the first force transducer element, the second force transducer element, and the third force transducer element, the data processing device configured to receive the first, second, and third quantities that are representative of the loads being applied to the first measurement surface, the second measurement surface, and transferred between the first and second plate components, respectively, and to convert the first, second, and third quantities into output loads.

9. The dual force plate system according to claim 1, wherein the first force transducer element and the second force transducer element each comprise one or more apertures disposed therein and one or more pluralities of strain gages disposed on outer surfaces thereof, the outer surfaces of each force transducer element on which each of the one or more pluralities of strain gages are disposed being generally opposite to an inner surface of each of the one or more apertures.

10. The dual force plate system according to claim 1, wherein a gap is provided between the first plate component and the second plate component so as to prevent interaction between the two plate components.

11. A force plate system comprising, in combination:
a force measurement assembly configured to receive a subject, the force measurement assembly including:
one or more surfaces for receiving both feet of the body of the subject;
at least one force transducer, the at least one force transducer configured to sense one or more measured quantities and output one or more signals that are representative of a load being applied to the one or more surfaces of the force measurement assembly by the subject; and
a data processing device configured to convert the one or more signals that are representative of the load being applied to the one or more surfaces of the force measurement assembly by the subject into an output load, the output load comprising at least one vertical force quantity and at least one shear force quantity, the data processing device being further configured to compute the center of gravity for the subject as a function of the at least one vertical force quantity, the at least one shear force quantity, a height of the subject;
wherein a ratio of the at least one shear force quantity to the at least one vertical force quantity is calculated by the data processing device when computing the center of gravity for the subject.

12. The force plate system according to claim 11, wherein the data processing device is further configured to compute the center of gravity for the subject as a function of the height of the subject multiplied by a constant value, and wherein the data processing device is additionally configured to compute the center of gravity for the subject by multiplying a multiplicative product of the constant value and the height of the subject by the ratio of the at least one shear force quantity to the at least one vertical force quantity.

13. The force plate system according to claim 11, wherein the data processing device is further configured to compute the center of gravity for the subject as a function of a center of pressure coordinate determined using the force measurement assembly.

14. The force plate system according to claim 13, wherein, when computing the center of gravity for the subject, the data processing device is further configured to add the center of pressure coordinate determined using the force measurement assembly to the multiplicative product of: (i) the ratio of the at least one shear force quantity to the at least one vertical force quantity, (ii) the height of the subject, and (iii) a constant value.

15. A method for determining the center of gravity for a subject disposed on a force measurement assembly, the method comprising the steps of:

providing a force measurement assembly configured to receive a subject thereon, the force measurement assembly including:
one or more surfaces for receiving both feet of the body of the subject;
at least one force transducer, the at least one force transducer configured to sense one or more measured quantities and output one or more signals that are representative of a load being applied to the one or more surfaces of the force measurement assembly by the subject;
providing a data processing device operatively coupled to the force measurement assembly, the data processing device configured to receive the one or more signals that are representative of the load being applied to the one or more surfaces of the force measurement assembly by the subject and to convert the one or more signals into an output load;
positioning both feet of the subject on the one or more surfaces of the force measurement assembly;
sensing, by utilizing the at least one force transducer, one or more measured quantities that are representative of a load being applied to the one or more surfaces of the force measurement assembly by the subject and outputting one or more signals representative thereof;
converting, by using the data processing device, the one or more signals that are representative of the load being applied to the one or more surfaces of the force measurement assembly by the subject into an output load, the output load comprising at least one vertical force quantity and at least one shear force quantity;
computing, by using the data processing device, the center of gravity for the subject as a function of the at least one vertical force quantity, the at least one shear force quantity, and a height of the subject; and
when computing the center of gravity for the subject, calculating a ratio of the at least one shear force quantity to the at least one vertical force quantity by using the data processing device.

16. The method according to claim 15, further comprising the steps of:
computing, by using the data processing device, the center of gravity for the subject additionally as a function of the height of the subject multiplied by a constant value; and
when computing the center of gravity for the subject, multiplying a multiplicative product of the constant value and the height of the subject by the ratio of the at least one shear force quantity to the at least one vertical force quantity by using the data processing device.

17. The method according to claim 15, further comprising the step of:
computing, by using the data processing device, the center of gravity for the subject additionally as a function of a center of pressure coordinate determined using the force measurement assembly.

18. The method according to claim 17, further comprising the step of:
when computing the center of gravity for the subject using the data processing device, adding the center of pressure coordinate determined using the force measurement assembly to the multiplicative product of: (i) the ratio of the at least one shear force quantity to the at least one vertical force quantity, (ii) the height of the subject, and (iii) a constant value.

* * * * *